United States Patent [19]

Pissiotas et al.

[11] Patent Number: 5,731,267
[45] Date of Patent: Mar. 24, 1998

[54] PYRAZOLE HERBICIDES

[75] Inventors: Georg Pissiotas, Lörrach, Germany; Kurt Nebel, Hochwald; Hans-Georg Brunner, Lausen, both of Switzerland

[73] Assignee: Novartis Corporation, Summit, N.J.

[21] Appl. No.: 820,758

[22] Filed: Mar. 19, 1997

[30] Foreign Application Priority Data

Mar. 19, 1996 [CH] Switzerland ............... 725/96

[51] Int. Cl.[6] .................. A01N 43/56; C07D 405/02
[52] U.S. Cl. .................. 504/280; 504/282; 548/364.4
[58] Field of Search ............ 548/364.4; 504/280, 504/282

[56] References Cited

FOREIGN PATENT DOCUMENTS 9206962  4/1992  WIPO.

OTHER PUBLICATIONS

Journal of Heterocyclic Chemistry, Bol. 21, Nr. 1, Jan. 1984, Provous, pp. 177–180. I.-P. Bachelet et al.

Cantegnil et al, *Chemical Abstracts*, vol. 124, No. 335, 658 (1996).

Primary Examiner—Robert W. Ramsuer
Attorney, Agent, or Firm—William A. Teoli, Jr.

[57] ABSTRACT

Compounds of the formula I

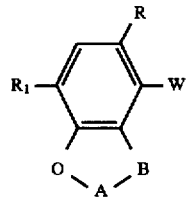

in which

R is hydrogen, fluorine or chlorine;

$R_1$ is hydrogen, halogen, trifluoromethyl, $C_1$–$C_4$haloalkoxy, cyano, nitro or amino;

A-B is a group

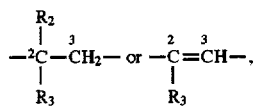

in which the 2 carbon atom is bonded to the oxygen atom;

W is a group

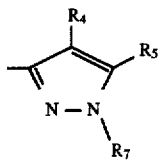

or

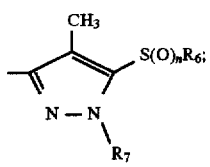

$R_2$ is hydrogen or $C_1$–$C_6$-alkyl;

$R_3$ is $C_1$–$C_6$alkyl, $C_1$–$C_6$haloalkyl, cyano-$C_1$–$C_4$alkyl, hydroxy-$C_1$–$C_6$alkyl, $C_1$–$C_6$alkoxy-$C_1$–$C_6$alkyl, $C_3$–$C_6$alkenyloxy-$C_1$–$C_4$-alkyl, $C_3$–$C_6$alkynyloxy-$C_1$–$C_4$alkyl, $C_1$–$C_6$alkylcarbonyloxy-$C_1$–$C_6$alkyl, carboxyl, $C_1$–$C_6$alkoxycarbonyl, $C_1$–$C_6$haloalkoxycarbonyl, $C_3$–$C_6$alkenyloxycarbonyl, $C_3$–$C_6$alkynyloxycarbonyl, $C_3$–$C_6$cycloalkoxycarbonyl, $C_1$–$C_4$alkoxy-$C_1$–$C_4$alkoxycarbonyl, $C_1$–$C_4$alkylaminocarbonyl, di-$C_1$–$C_4$alkylaminocarbonyl, aminocarbonyl, benzyloxycarbonyl, phenyloxycarbonyl, $C_1$–$C_4$alkyl-$SO_2NHC(O)$—, $C_1$–$C_6$alkyl -ON=CH—, $C_1$–$C_6$alkoxycarbonyl-$C_1$–$C_4$alkyl, $C_1$–$C_3$alkylcarbonyl, ClC(O)—, $NH_2C(S)$—, OHC— or cyano;

$R_4$ is hydrogen, fluorine, chlorine or bromine;

$R_5$ is carboxyl, $C_1$–$C_6$alkoxycarbonyl, $NH_2C(O)$—, $NH_2C(S)$—, HON=CH—, OHC— or cyano;

$R_6$ is hydrogen or $C_1$–$C_4$alkyl;

n is 0, 1 or 2, with the proviso that n is 0 if $R_6$ is hydrogen; and $R_7$ is hydrogen or $C_1$–$C_4$alkyl, and agronomically acceptable salts and stereoisomers of these compounds are suitable as herbicides.

26 Claims, No Drawings

PYRAZOLE HERBICIDES

The invention relates to novel herbicidally active benzofuranyl- and dihydrobenzofuranyl-substituted pyrazole derivatives, to processes for their preparation, to compositions comprising these compounds and to their use for controlling weeds, mainly in crops of useful plants, or for inhibiting plant growth.

Benzofuranyl- and dihydrobenzofuranyl-substituted uracils, phthalimides, oxadiazolones, triazolones, triazinediones and imidazolidinediones which are herbicidally active are described, for example, in U.S. Pat. No. 4,881,967, EP-A-0 271 170, EP-A-0 476 697, EP-A-0 561 319, EP-A-0 617 033 and WO 95/05079.

There have now been found novel benzofuranyl- and dihydrobenzofuranyl-substituted pyrazole derivatives which have herbicidal and growth-inhibitory properties.

The present invention therefore relates to compounds of the formula I

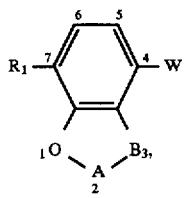

in which

R is hydrogen, fluorine or chlorine;

$R_1$ is hydrogen, halogen, trifluoromethyl, $C_1$-$C_4$haloalkoxy, cyano, nitro or amino;

A-B is a group

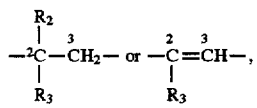

in which the 2 carbon atom is bonded to the oxygen atom;

W is a group

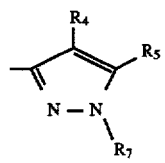

or

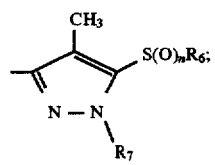

$R_2$ is hydrogen or $C_1$-$C_6$alkyl;

$R_3$ is $C_1$-$C_6$alkyl, $C_1$-$C_6$haloalkyl, cyano-$C_1$-$C_4$alkyl, hydroxy-$C_1$-$C_6$alkyl, $C_1$-$C_6$alkoxy-$C_3$-$C_6$alky, $C_3$-$C_6$alkenyloxy-$C_1$-$C_4$-alkyl, $C_3$-$C_6$alkynyloxy-$C_1$-$C_4$alkyl, $C_1$-$C_6$alkylcarbonyloxy-$C_1$-$C_6$alkyl, carboxyl, $C_1$-$C_6$alkoxycarbonyl, $C_1$-$C_6$haloalkoxycarbonyl, $C_3$-$C_6$alkenyloxycarbonyl, $C_3$-$C_6$alkynyloxycarbonyl, $C_3$-$C_6$cycloalkoxycarbonyl, $C_1$-$C_4$alkoxy-$C_1$-$C_4$alkoxycarbonyl, $C_1$-$C_4$alkylaminocarbonyl, di-$C_1$-$C_4$alkylaminocarbonyl, aminocarbonyl, benzyloxycarbonyl, phenyloxycarbonyl, $C_1$-$C_4$alkyl-$SO_2NHC(O)$—, $C_1$-$C_6$alkyl-ON=CH—, $C_1$-$C_6$alkoxycarbonyl-$C_1$-$C_4$alkyl, $C_1$-$C_3$alkylcarbonyl, ClC(O)—, $NH_2C(S)$—, OHC— or cyano;

$R_4$ is hydrogen, fluorine, chlorine or bromine;

$R_5$ is carboxyl, $C_1$-$C_6$alkoxycarbonyl, $NH_2C(O)$—, $NH_2C(S)$—, HON=CH—, OHC— or cyano;

$R_6$ is hydrogen or $C_1$-$C_4$alkyl;

n is 0, 1 or 2, with the proviso that n is 0 if $R_6$ is hydrogen; and $R_7$ is hydrogen or $C_1$-$C_4$alkyl;

and to agronomically acceptable salts and stereoisomers of these compounds.

The alkyl groups which occur in the definitions of the substituents can be straight-chain or branched, and this also applies to the alkyl moiety of the haloalkyl, alkyl-$SO_2NHC$ (O), alkyl-ON=CH, alkylaminocarbonyl, dialkylaminocarbonyl, cyanoalkyl, hydroxyalkyl and alkylcarbonyl groups.

Alkyl groups are, for example, methyl, ethyl, n-propyl, isopropyl, n-butyl, sec-butyl, isobutyl, tert-butyl, and the various isomeric pentyl and hexyl radicals. Methyl, ethyl, n-propyl, isopropyl and n-butyl are preferred.

Halogen is to be understood as meaning iodine and, preferably, fluorine, chlorine and bromine.

Suitable haloalkyl groups are alkyl groups which are mono- or polysubstituted, in particular mono-, di- or trisubstituted, by halogen, halogen being, specifically, iodine and in particular fluorine, chlorine and bromine, for example fluoromethyl, difluoromethyl, trifluoromethyl, chloromethyl, dichloromethyl, trichloromethyl, 2,2-difluoroethyl, 2-fluoroethyl, 2-chloroethyl and 2,2-dichloroethyl.

The alkenyl and alkynyl groups may be straight-chain or branched, and this also applies to the alkenyl and alkynyl moiety of the alkenyloxyalkyl, alkynyloxyalkyl, alkenyloxycarbonyl and alkynyloxycarbonyl groups.

Alkenyloxyalkyl is, for example, allyloxyalkyl, methallyloxyalkyl and but-2-en-1-yloxyalkyl.

Alkynyloxyalkyl is, for example, propargyloxyalkyl and 1-methylpropargyloxyalkyl.

Alkenyloxycarbonyl is, for example, allyloxycarbonyl, methallyloxycarbonyl, but-2-en-1-yl-oxycarbonyl, pentenyloxycarbonyl and 2-hexenyloxycarbonyl.

Alkynyloxycarbonyl is, for example, propargyloxycarbonyl, 3-butynyloxycarbonyl, but-2-yn-1-yl-oxycarbonyl and 2-methylbutyn-2-yl-oxycarbonyl.

Alkylaminocarbonyl is, for example, methylaminocarbonyl, ethylaminocarbonyl and the isomeric propyl- and butylaminocarbonyl radicals.

Dialkylaminocarbonyl is, for example, dimethylaminocarbonyl, diethylaminocarbonyl and the isomeric dipropyl- and dibutylaminocarbonyl radicals.

Alkoxyalkoxycarbonyl is, for example, methoxymethoxycarbonyl, ethoxymethoxycarbonyl, ethoxyethoxycarbonyl, propoxymethoxycarbonyl, propoxyethoxycarbonyl, propoxypropoxycarbonyl and butoxyethoxycarbonyl.

Haloalkoxy is, for example, fluoroethoxy, difluoroethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

The cycloalkoxycarbonyl radicals which are suitable as substituents are, for example, cyclopropyloxycarbonyl, cyclobutyloxycarbonyl, cyclopentyloxycarbonyl and cyclohexyloxycarbonyl.

Analogous meanings can also be allocated to the substituents in composite definitions, for example haloalkoxy, alkoxycarbonylalkyl, alkoxyalkoxycarbonyl, alkylcarbonyloxyalkyl, alkoxycarbonyl, alkoxyalkyl and haloalkoxycarbonyl.

The invention also encompasses the salts which the compounds of the formula I which have an azidic hydrogen, in particular derivatives with carboxyl and sulfonamide groups (for example carboxyl- and alkyl-SO$_2$NHC(O)-substituted benzofuranyl- and dihydrobenzofuranylpyrazolyl groups) may form with bases. These salts are, for example, alkali metal salts, for example sodium and potassium salts; alkaline earth metal salts, for example calcium and magnesium salts; ammonium salts, i.e. unsubstituted ammonium salts and mono- or polysubstituted ammonium salts, for example triethylammonium and methylammonium salts; or salts with other organic bases.

Salt formers which must be emphasized amongst the alkali metal hydroxides and alkaline earth metal hydroxides are the hydroxides of lithium, sodium, potassium, magnesium or calcium, but in particular those of sodium and potassium.

Possible examples of amines which are suitable for ammonium salt formation are not only ammonia, but also primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylendiamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines, for example pyridine, quinoline, isoquinoline, morpholine, thiomorpholine, piperidine, pyrrolidine, indoline, quinuclidine and azepine; primary arylamines, for example anilines, methoxyanilines, ethoxyanilines, o,m,p-toluidines, phenylendiamines, benzidines, naphthylamines and o,m,p-chloroanilines but in particular triethylamine, isopropylamine and di-isopropylamine.

The salts of the compounds of the formula I which have basic groups, in particular basic pyrazolyl rings W1 or W2, or of the derivatives which have amino groups, for example aniline derivatives when $R_1$= amino are, for example, salts with inorganic and organic acids, for example hydrohalic acids such as hydrofluoric acid, hydrochloric acid, hydrobromic acid or hydroiodic acid, and also sulfuric acid, phosphoric acid, nitric acid, and organic acids such as acetic acid, trifluoroacetic acid, trichloroacetic acid, propionic acid, glycolic acid, thiocyanic acid, citric acid, benzoic acid, oxalic acid, formic acid, benzenesulfonic acid, p-toluenesulfonic acid and methanesulfonic acid.

The possible presence of at least one asymmetric carbon atom in the compounds of the formula I, for example in the dihydrobenzofuranyl moiety on the 2 carbon atom or in the alkyl moiety of the substituent $R_3$ results in the fact that the compounds can occur not only in the form of optically active individual isomers, but also in the form of racemic mixtures. In the present invention, the active ingredients of the formula I are to be understood as meaning not only the pure optical antipodes, but also the racemates or diastereomers.

If an aliphatic C=C— or C=N—O double bond (syn/anti) is present, geometric isomerism may occur. The present invention also encompasses these isomers.

Preferred compounds of the formula I are those in which $R_1$ is hydrogen, fluorine, chlorine, bromine, trifluoromethyl or cyano.

Other preferred compounds of the formula I are those in which R is hydrogen or fluorine.

Especially preferred amongst these compounds are those in which R is fluorine.

Other preferred compounds of the formula I are those in which W is a group

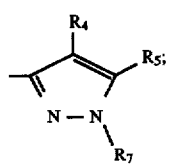

(W1)

and $R_4$, $R_5$ and $R_7$ are as defined in the formula I.

Especially preferred amongst the above are, in particular, those in which $R_7$ is hydrogen, methyl or ethyl.

Equally, especially preferred compounds of the formula I are those in which $R_5$ is carboxyl, $C_1$–$C_3$alkoxycarbonyl, NH$_2$C(S)—, HON=CH—, OHC— or cyano.

Very especially preferred compounds of the formula I of the above are those in which $R_5$ is cyano.

Other especially preferred compounds of the formula I are those in which $R_4$ is hydrogen or chlorine.

Equally preferred compounds of the formula I are those in which W is a group

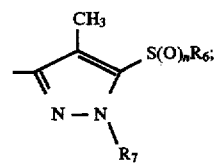

(W2)

and $R_6$, $R_7$ and n are as defined under formula I.

Especially preferred compounds amongst the above are those in which n is 0 or 2.

Other especially preferred compounds of the formula I are those in which $R_6$ is methyl.

Furthermore, especially preferred compounds of the formula I are those in which $R_7$ is methyl or ethyl.

Very especially preferred amongst the above are, in particular, those in which $R_7$ is methyl.

Important compounds of the formula I are those in which A-B is a group

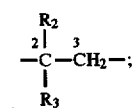

$R_2$ is hydrogen or methyl; and $R_3$ is hydrogen, $C_1$$C_3$alkyl, $C_1$- or $C_2$haloalkyl, cyano-$C_1$–$C_4$alkyl, $C_1$–$C_3$alkylcarbonyloxy-$C_1$— or —$C_2$alkyl, carboxyl, $C_1$–$C_3$alkoxycarbonyl, $C_1$–$C_3$alkyl-ON=CH—, $C_1$–$C_3$alkoxycarbonyl-$C_1$— or —$C_2$alkyl, $C_1$–$C_3$alkylcarbonyl or OHC—.

The process according to the invention for the preparation of compounds of the formula I is carried out analogously to known processes and, in order to prepare those compounds of the formula I in which A-B is a group

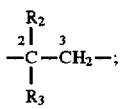

$R_2$ is as defined under formula I; and $R_3$ is $C_1$–$C_6$alkyl, comprises reacting a compound of the formula II

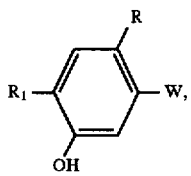

in which R, $R_1$ and W are as defined under formula I with a compound of the formula III

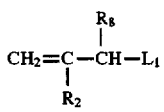

in which $R_2$ is as defined above; $R_8$ is hydrogen or $C_1$–$C_5$alkyl; and $L_1$ is a leaving group, for example halogen, in particular bromine or chlorine, if appropriate in the presence of an inert organic solvent and of a base, to give the compound of the formula IVa

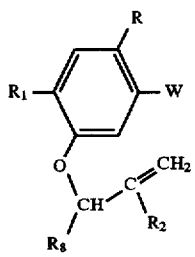

in which R, $R_1$, $R_2$, $R_8$ and W are as defined above, subjecting this compound to a rearrangement reaction, either with exposure to heat or with acid catalysis, to give the compound of the formula Va

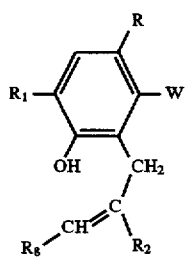

and subsequently cyclizing the latter.

Another process according to the invention for the preparation of compounds of the formula I is carried out analogously to known processes and, in order to prepare those compounds of the formula I in which A-B is a group

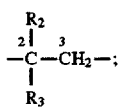

$R_2$ is as defined under formula I; and $R_3$ is hydroxy-$C_1$–$C_6$alkyl, comprises epoxidizing a compound of the formula Va

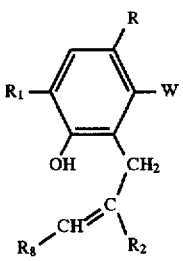

in which R, $R_1$, $R_2$ and W are as defined under formula I; and $R_8$ is hydrogen or $C_1$–$C_5$alkyl, and subsequently, if desired, cyclizing the product in the presence of a catalyst.

The process according to the invention for the preparation of compounds of the formula I is carried out analogously to known processes and, in order to prepare those compounds of the formula I in which A-B is a group

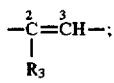

and $R_3$ is $C_1$–$C_6$alkyl, comprises subjecting the compound of the formula IVb

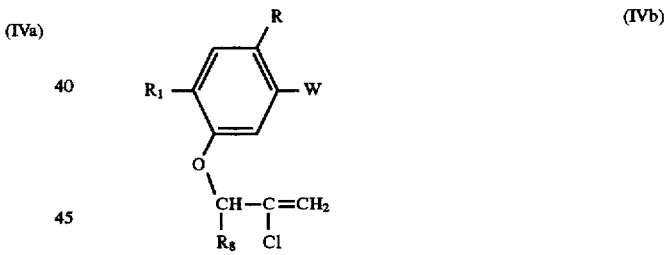

in which R, $R_1$ and W are as defined under formula I; and $R_8$ is hydrogen or $C_1$–$C_5$alkyl to a rearrangement reaction with exposure to heat to give the compound of the formula Vb

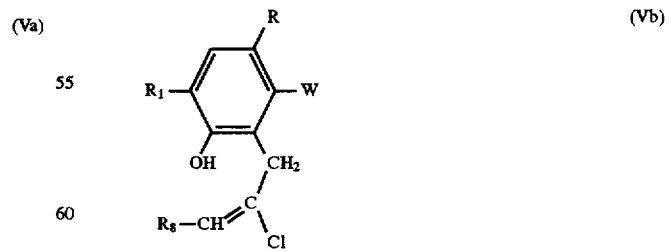

and subsequently cyclizing the latter.

The process according to the invention for the preparation of compounds of the formula I is carried out analogously to known processes and, in order to prepare those compounds of the formula I in which W is a group

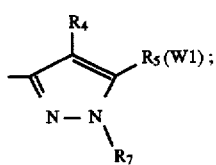

$R_4$ is hydrogen, fluorine, chlorine or bromine; $R_5$ is $C_1$–$C_6$alkoxycarbonyl, $NH_2C(O)$— or cyano; and $R_7$ is hydrogen or $C_1$–$C_4$alkyl, comprises diazotizing a compound of the formula VI

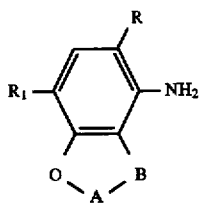

in which R, $R_1$ and A-B have the meanings given under formula I, replacing the diazonium group by a halogen in the presence of a copper(I) salt, thus obtaining the compound of the formula VII

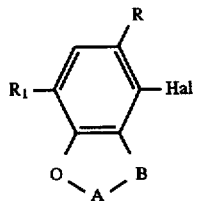

in which Hal is halogen, reacting this compound in the presence of palladium(II) chloride, triphenylphosphine and n-butyl vinyl ether to give the compound of the formula VIII

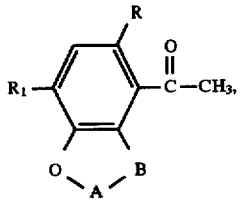

subsequently reacting this compound with a dialkyloxalate of the formula IX

in which $R_9$ is $C_1$–$C_6$alkyl, preferably dimethyl phthalate, in the presence of a base, in particular the corresponding sodium alkoxide, preferably sodium methoxide, in a solvent, for example the corresponding alcohol, preferably methanol, to give the compound of the formula X

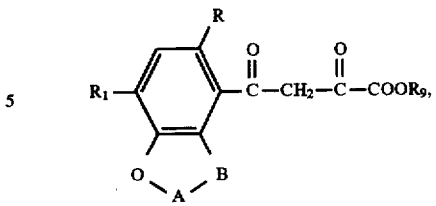

cyclizing the latter in the presence of hydrazine to give the compound of the formula Ia

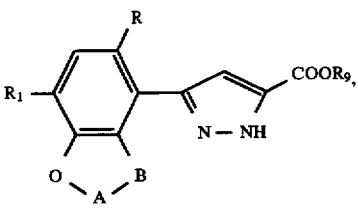

subsequently converting the latter first with an alkylating reagent of the formula XIIa $$R_7\text{—}L_2 \quad (XIIa)$$

or of the formula XIIb $$R_7OSO_2OR_7 \quad (XIIb)$$

where the radical $R_7$ in the compounds of the formulae XIIa and XIIb is $C_1$–$C_4$alkyl and $L_2$ is a leaving group, preferably chlorine, bromine, iodine, $CH_3SO_2O$— or

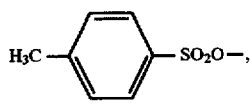

to give the compound of the formula Ib

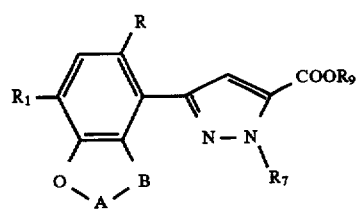

in which R, $R_1$, $R_7$, $R_9$ and A-B are as defined above, and subsequently subjecting the product to a halogenation reaction, thus obtaining the compound of the formula Ic

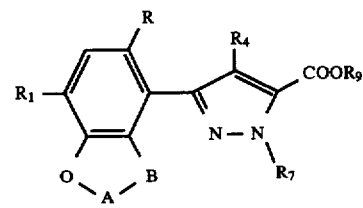

in which R, $R_1$, $R_7$, $R_9$ and A-B are as defined above; and $R_4$ is fluorine, chlorine or bromine, and reacting this compound either directly or via the corresponding carboxylic acid or the corresponding carboxylic acid halide of the formula $Ic_1$

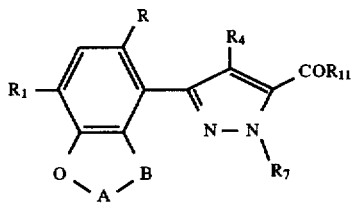
(Ic₁)

in which R, R₁, R₄, R₇ and A-B are as defined above; and R₁₁ is hydroxyl or halogen, preferably chlorine, with ammonia to give the amide of the formula Id

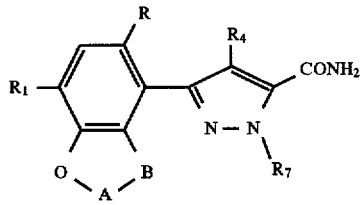
(Id)

and subsequently dehydrating the latter.

The process according to the invention for the preparation of the compounds of the formula I is carried out analogously to known processes and, in order to prepare those compounds of the formula I in which W is a group

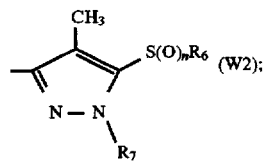
(W2);

and R₆, R₇ and n are as defined under formula I, comprises a) cyclizing a compound of the formula XI

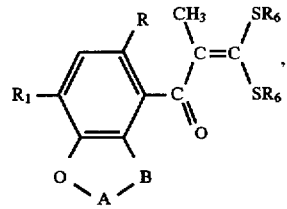
(XI)

In which R, R₁, R₆ and A-B are as defined under formula I with hydrazine, in the presence or absence of a suitable solvent, to give the compound of the formula Ie

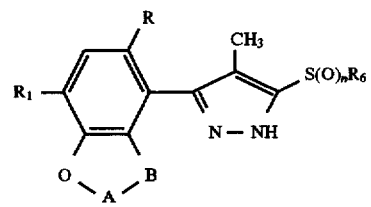
(Ie)

in which n is 0 and subsequently reacting this compound with a compound of the formula XIIa R₇—L₂ (XIIa)

or of the formula XIIb

R₇OSO₂OR₇ (XIIb), the radical R₇ in the compounds of the formulae XIIa and XIIb being C₁-C₄alkyl and L₂ being a leaving group, preferably chlorine, bromine, iodine, CH₃SO₂O— or

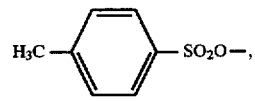

to give a compound of the formula If

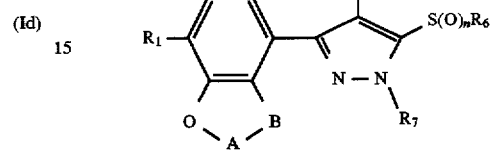
(If)

in which R, R₁, R₆, R₇ and A-B are as defined above; and n is 0, and subsequently oxidizing the product; or b) cyclizing a compound of the formula XI

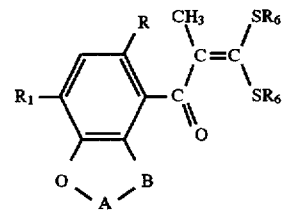
(XI)

in which R, R₁, R₆, R₇ and A-B are as defined in the formula I with a compound of the formula XIII

NH₂—NH—R₇ (XIII)

in which R₇ is as defined above, in the presence or absence of a suitable solvent, to give the compound of the formula If and subsequently oxidizing this compound.

A further process according to the invention for the preparation of compounds of the formula I is carried out analogously to known processes and comprises, in order to prepare those compounds of the formula I in which W is a group

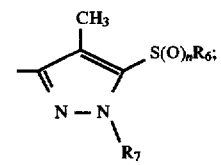
(W2)

R₇ is hydrogen; and R₆ and n are as defined under formula I, halogenating a compound of the formula VIIIa

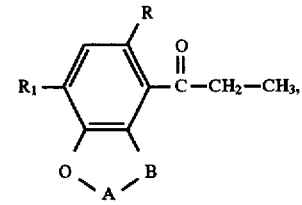
(VIIIa)

in the presence or absence of a solvent and of a base, to give the compound of the formula XIV

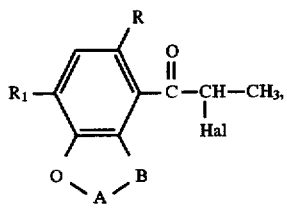

(XIV)

R, $R_1$ and A-B in the compounds of the formulae VIIIa and XIV being as defined in formula I and Hal being halogen, preferably chlorine or bromine and cyclizing this compound with the compound of the formula XV $$NH_2-NH-C(S)S-R_6 \quad (XV)$$

in which $R_6$ is as defined above, in the presence or absence of a solvent and of a base, to give the compound of the formula XVI

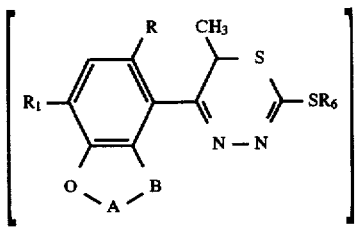

(XVI)

and subjecting the latter to a ring contraction (n=0), either with exposure to heat or with acid catalysis, and subsequently oxiding the product (n=1 or 2).

The synthesis of the benzofuran and dihydrobenzofuran rings of the compounds of the formula I is illustrated in greater detail in equations 1, 2 and 3 below.

Equation 1

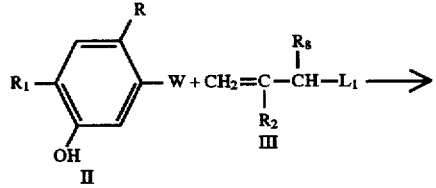

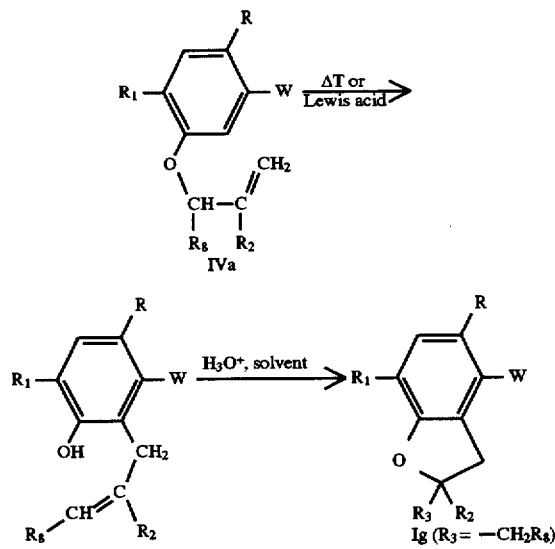

Equation 2

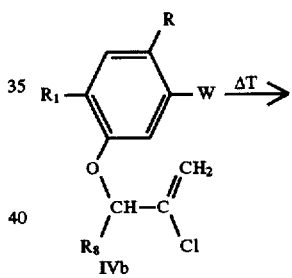

Equation 3

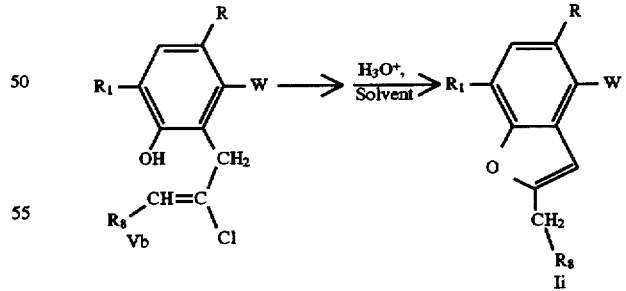

The synthesis of the pyrazole rings W1 and W2 of the compounds of the formula I is illustrated in greater detail in Equations 4, 5 and 6 below.

Equation 4
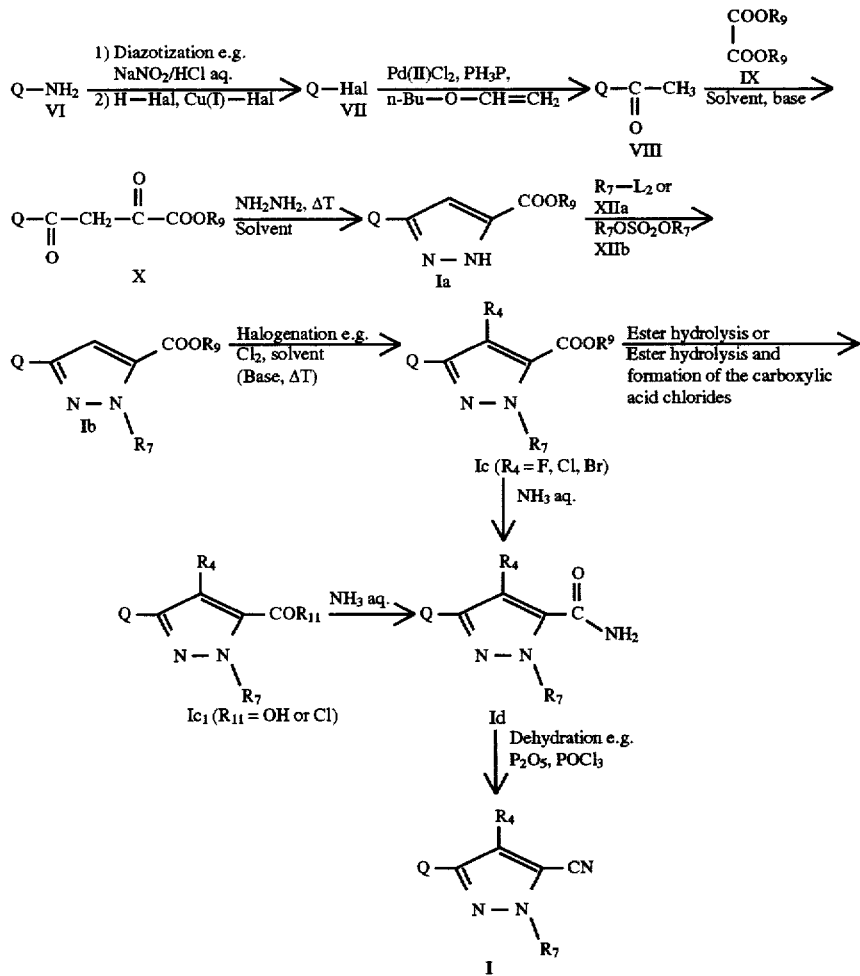
Equation 5
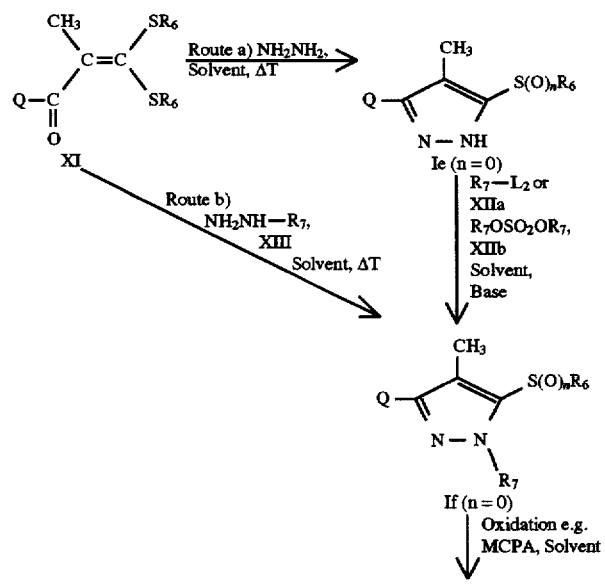

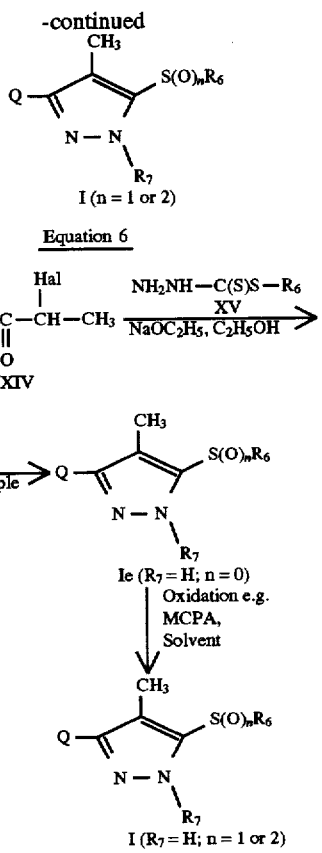

Equation 6

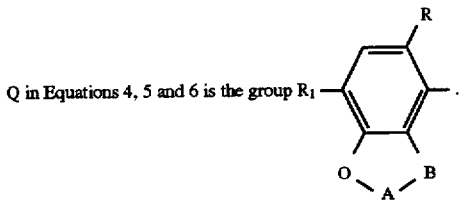

Q in Equations 4, 5 and 6 is the group

The allyl ethers of the formula IVa can be obtained in accordance with Equation 1, for example analogously to EP-A-0 617 033 (page 3, lines 45 and 46) or U.S. Pat. No. 4,881,967 (column 11, lines 17–39) by reacting the compounds of the formula II with an allyl derivative of the formula III in which $L_1$ is a leaving group, for example halogen, in particular chlorine or bromine, if appropriate in an inert organic solvent, for example acetone, acetonitrile or N,N-dimethylformamide, in the presence of a base, for example potassium carbonate.

The allylated phenol derivatives of the formula Va are obtained from the corresponding allyl ethers of the formula IVa by means of a rearrangement reaction and exposure to heat. This rearrangement reaction (Claisen rearrangement) is carried out for example analogously to EP-A-0 617 033 (page 3, lines 17–44) or U.S. Pat. No. 4,881,967 (column 10, line 30 to end of column 10), in the presence or absence of a solvent such as toluene, xylenes, mesitylene or tetralin and tertiary amines, for example N,N-diethylaniline, or mixtures of these at temperatures from 20° C. to 300° C., preferably at 100° C. to 250° C., in the course of 0.5 to 48 hours. The rearrangement reaction may be carried out, if desired, in a sealed pressurized container.

Alternatively, this rearrangement reaction can also be carried out in the presence of a Lewis acid catalyst, for example boron trichloride, in an inert solvent, for example dichloromethane, at temperatures from 0° C. to 25° C., for example analogously to U.S. Pat. No. 4,881,967 (column 10, line 66 to end of column 10, and column 11, lines 1–7).

The subsequent cyclization reaction of the compounds of the formula Va can be carried out by one or more methods as described, for example, in U.S. Pat. No. 4,881,967 (column 8, lines 56 to end of column 8, and column 9, lines 1–3), but in particular with acid catalysis in an inert organic solvent, for example xylenes, in the presence of acids, for example p-toluenesulfonic acid.

The preparation of the compounds of the formula I in which $R_3$ is hydroxy-$C_1$-$C_6$alkyl ($R_3$=—CH(OH)—$R_8$) is carried out in accordance with Equation 2 by epoxidizing the compound of the formula Va, for example using m-chloroperbenzoic acid (MCPA), in the presence of an organic solvent, followed by cyclization analogously to, for example, EP-A-0 617 033 (page 3, last section, and page 4, lines 1–50).

The allyl ethers of the formula IVb in Equation 3 can be obtained, for example, analogously to EP-A-0 561 319 from the corresponding phenols of the formula II and the allyl derivatives of the formula III (Equation 1; $R_2$=chlorine).

The phenols of the formula Vb can be obtained by heating the allyl ethers of the formula IVb analogously to the procedure described for Equation 1. This rearrangement is carried out with exposure to heat at temperatures from 150° C. to 250° C. in the course of 2 to 100 hours, in the presence or absence of an inert organic solvent.

The subsequent cyclization of the phenols of the formula Vb is expediently carried out in the presence of an acid, for example mineral acids such as hydrochloric acid, sulfuric acid or polyphosphoric acid, organic acids such as p-toluenesulfonic acid or trifluoromethanesulfonic acid and also carboxylic acids such as formic acid, acetic acid or trifluoroacetic acid. The amount of acid used relative to phenols of the formula Vb is 1.1:1 to 100:1.

This cyclization reaction is carried out in the presence or absence of a solvent, for example aromatic hydrocarbons such as benzene or toluene, halogenated hydrocarbons such as chloroform or carbon tetrachloride, mineral acids such as hydrochloric acid or sulfuric acid, organic acids such as acetic acid, and water. Mixtures of these solvents may also be employed.

This cyclization is successfully carried out at temperatures from 0° C. to 100° C., preferably from 5° C. to 80° C., in the course of 0.5 to 24 hours.

All further functionalization reactions of the substituent $R_3$ (or —$CH_2R_8$ or —CH(OH)—$R_8$) in the 2-position of the benzofuranyl or dihydrobenzofuranyl increment to give the compounds of the formula I can be carried out analogously to the procedure described, for example, in EP-A-0 617 033 (page 3, last section, to page 8), EP-A-0 561 319 (page 3, last section, to page 10) or U.S. Pat. No. 4,881,967 (columns 13 and 14), starting from the compounds of the formula Ii or Ig and Ih in Equations 1, 2 and 3.

The starting material for the preparation of the pyrazole rings of the compounds of the formula I in which W is a group

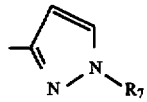

(W1)

are, in accordance with Equation 4, the aniline derivatives of the formula VI. These may be used to obtain the 4-halobenzofurans and -dihydrobenzofuran derivatives, in particular the 4-bromobenzofuran and -dihydrobenzofuran derivatives of the formula VII, by diazotization following standard methods, for example with sodium nitrite in aqueous hydrochloric acid and reaction of the resulting diazonium salt with hydrohalic acid such as hydrobromic acid in the presence of a copper(I) salt such as copper bromide (Sandmeyer reaction).

The further reaction of the halogenated benzofuran or dihydrobenzofuran derivatives of the formula VII in the presence of palladium(11) chloride, triphenylphosphine and n-butyl vinyl ether is carried out for example analogously to Indian J. Chem. B 31,363 (1992), giving the acetophenone derivatives of the formula VIII.

These are subsequently reacted with a dialkyl oxalate, preferably dimethyl oxalate, in the presence of a base, in particular the corresponding sodium alkoxide, preferably sodium methoxide, in a solvent such as the corresponding alcohol, preferably methanol, together with a secondary solvent such as an ether or hydrocarbon at temperatures of from 0° C. to the boiling point of the solvent in question.

This condensation reaction and all subsequent reaction steps up to the 5-nitrilopyrazole derivatives of the formula I in accordance with Equation 4 can be carried out analogously to the procedure described in, for example, WO 96/01254 (page 20 et seq.).

In accordance with this equation, the diketo esters of the formula X are cyclized with hydrazine at elevated temperature (reflux), preferably in glacial acetic acid, toluene or an alcohol as the solvent, to give the compounds of the formula Ia. If desired, an acid such as sulfuric acid or p-toluenesulfonic acid can be employed as the catalyst.

The N-alkylation of the pyrazoles of the formula Ia is carried out for example analogously to the procedure described in WO 96/01254, pages 20 and 34 et seq., at 22° C. or moderately elevated temperatures in the presence of a solvent such as acetone, methyl ethyl ketone, N,N-dimethylformamide, N-methylpyrrolidone or dimethylsulfoxide, a base such as sodium carbonate, potassium carbonate, sodium hydroxide or potassium hydroxide, and of an alkylating agent of the formula XIIa or XIIb, preferably methyl iodide or dimethyl sulfate.

The subsequent halogenation in the 4-position of the pyrazole ring ($R_4$) in accordance with Equation 4 is carried out for example analogously to WO 96/01254, page 23 and 37 et seq., by means of a dihalogen molecule, preferably $Cl_2$, $Br_2$, $I_2$, F—I or Cl—I, the last two reagents preferentially forming the iodide derivative, in a suitable solvent, preferably glacial acetic acid or carbon tetrachloride at temperatures of from 10° C. to the reflux temperature of the reaction mixture in question. In certain cases, it is advantageous to halogenate in the presence of a base, for example sodium acetate, it being possible to add the base before or else during the halogenation. To accelerate the halogenation, a catalyst such as aluminium chloride, iron(II) chloride or iron powder, may be added to the reaction mixture, if desired.

The subsequent conversion of the ester derivatives of the formula Ic into the corresponding amides of the formula Id in accordance with Equation 4 can be carried out for example either directly by heating the ester derivatives in aqueous ammonia or, alternatively, by hydrolysis of the ester derivatives of the formula Ic to give the corresponding carboxylic acid derivatives of the formula $Ic_1$ ($R_{11}$=OH) followed by heating the resulting carboxylic acid derivatives in aqueous ammonia or via converting the carboxylic acid derivatives of the formula $Ic_1$ ($R_{11}$=OH) into the corresponding carboxylic acid halides of the formula $Ic_1$ ($R_{11}$=Halogen, in particular chlorine) followed by heating the resulting carboxylic acid halides in aqueous ammonia.

The desired 4-nitrilopyrazole derivatives of the formula I can be obtained by dehydrating the amides of the formula Id which have been formed as described above, for example analogously to the method described in WO 96/01254, pages 23 and 41 et seq. and 'Advanced Organic Chemistry', Editor J. March, McGraw-Hill Book Company, N.Y., 1985, page 932 et seq.

The pyrazole ring of the compounds of the formula I in which W is a group

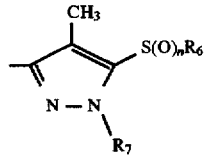

(W2)

(Equation 5, route a)) is synthesized by reacting the compounds of the formula XI with hydrazine or hydrazine hydrate, if appropriate in the presence of a suitable solvent at elevated temperature, preferably with hydrazine hydrate in alcoholic solution at elevated temperature ($R_7$=hydrogen).

To synthesize the pyrazole rings which are substituted on the nitrogen atom ($R_7$=$C_1$–$C_4$alkyl; Equation 5, route b)), the procedure is as described for Equation 5, route a), the reagent employed being the compound of the formula XIII, for example N-alkylhydrazine, preferably N-methylhydrazine.

In Equation 5, route b), the radical $R_7$ in the hydrazine derivative of the formula XIII and in the alkylating agents of the formulae XIIa and XIIb (Equation 5, route a)) is $C_1$–$C_4$alkyl, and $L_2$ is a leaving group such as chlorine, bromine, iodine, $CH_3SO_2O$— or

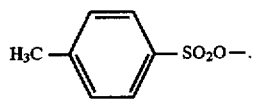

The N-alkylation of the pyrazole rings in the compounds of the formula Ie in Equation 5 is carried out at room temperature or moderately elevated temperatures in the presence of a solvent such as acetone, methyl ethyl ketone, N,N-dimethylformamide, N-methylpyrrolidone or dimethyl sulfoxide, of a base such as potassium carbonate, sodium carbonate, sodium hydroxide or potassium hydroxide, and an alkylating agent of the formula XIIa or XIIb, preferably methyl iodide or dimethyl sulfate.

The pyrazole rings of the formulae I and Ie which are unsubstituted on the nitrogen atoms (Equation 6) can also be synthesized for example by halogenating the compounds of the formula VIIIa, preferably using chlorine or bromine, in the presence or absence of a suitable solvent and of a base such as acetic acid and sodium acetate, subsequently cyclizing the product with a compound of the formula XV, if appropriate in a solvent such as an alcohol, preferably ethanol, and in the presence of a base, for example an alkoxide, preferably ethoxide, and by ring contraction (extrusion reaction) in analogy to known processes for example those described in Chem. Ber. 92, 2593 (1959) or Acta Chem. Scand. 16, 2395 (1962). This method, which is described in Equation 6, is suitable for the preparation of derivatives of the formula Ie or I which are halogen-substituted, in particular fluorine- or chlorine-substituted, on the phenyl ring.

The choice of a suitable preparation method and the respective reaction conditions depends on the properties (reactivities) of the substituents in the intermediates in question.

The subsequent oxidation of the compounds of the formulae Ie and If in which n is 0 (Equations 5 and 6) is carried out for example with peracids, for example m-chloroperbenzoic aid (MCPA) or hydrogen peroxide in the presence of a suitable solvent, for example dichloromethane, chloroform or carbon tetrachloride, at temperatures of from –40° C. to the reflux temperature of the solvent in question, preferably from 0° C. to 35° C. The degree of oxidation on the sulfur atom can be controlled by the amount of oxidant: equimolar amounts of oxidant give compounds of the formula I where n is 1, and an excess (at least 2 moles) of oxidant with compounds of the formula I where n is 2.

The starting compound of the formula XI in Equation 5 can be prepared analogously to known processes, for example in accordance with the method given in Equation 7 below.

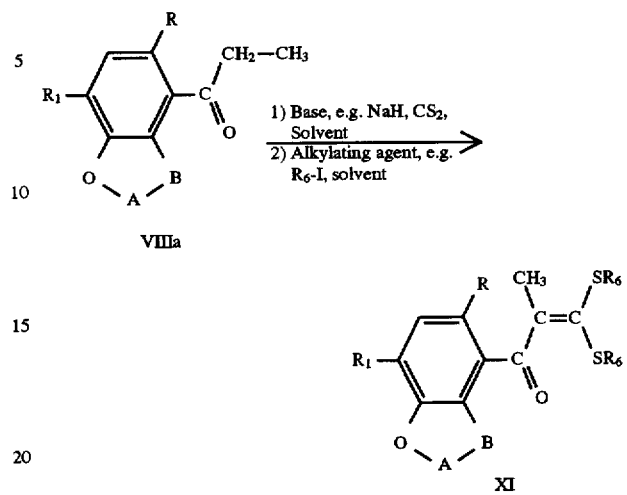

The reaction in Equation 7 is carried out for example analogously to WO 92/02509. In accordance with this publication, the ketone derivative of the formula VIIIa is reacted with carbon disulfide at temperatures of from 0° C. to 80° C. in the presence of a base, for example sodium hydride or potassium tert-butoxide, and of an aprotic solvent, for example tetrahydrofuran, followed by the immediate addition of an alkylating agent, for example $R_6$-Hal or $R_6OSO_2OR_6$, where $R_6$ is as defined under formula I and Hal is halogen, in particular chlorine, bromine or iodine, at temperatures of from 0° C. to the reflux temperature of the solvent used.

The compounds of the formula XV in Equation 6 can be prepared by known methods (for example Chem. Ber. 92, 2593 (1959) or Acta Chem. Scand. 16, 2395 (1962)), for example by reacting hydrazine or hydrazine hydrate with carbon disulfide followed by alkylation with the reagent $R_6$-Hal or $R_6OSO_2OR_6$ in which $R_6$ is as defined under formula I and Hal is halogen, in particular chlorine or bromine, in the presence of a base. Examples of suitable solvents are alcohols, for example ethanol, and examples of suitable bases are alkoxides, for example sodium methoxide or sodium ethoxide, or potassium hydroxide or sodium hydroxide.

The starting compounds of the formula VIIIa in Equation 7 can be carried out analogously to known process, for example following the method given in Equation 8 below.

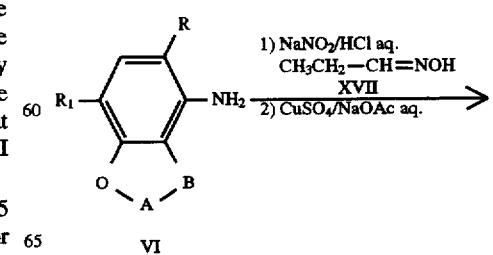

-continued
Equation 8

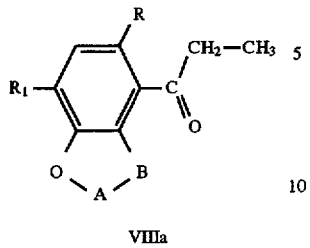

VIIIa

In Equation 8, the radicals R, R₁ and A-B are as defined under formula I, but it must be borne in mind that not all definitions of substituents are compatible with the process given. The choice of a suitable preparation method depends on the properties (reactivities) of the substituents in the intermediates in question.

The reaction in accordance with Equation 8 is carried out analogously to J. Chem. Soc. 1954, 1297. In accordance with this publication, the amines of the formula VI are first diazotized to give the corresponding diazonium salts and reacted with the propionaldehyde oxime of the formula XVII. Subsequent hydrolysis, for example with aqueous sodium acetate and copper sulfate, yields the corresponding ketone derivative of the formula VIIIa.

Other preparation methods for the starting compounds of the formula VIIIa can be carried out starting from the corresponding benzofuran or dihydrobenzofuran derivative via Lewis-acid-catalyzed acylation, for example analogously to 'Vogel's Textbook of Practical Organic Chemistry', Longman 1989, page 1006 et seq.;

or starting from the corresponding benzofuran- or dihydrobenzofurancarboxylic acid derivative via reaction with ethyllithium or ethylmagnesium chloride or ethylmagnesium bromide, for example analogously to Organic Reactions 18, 1 (1970); Organic Synthesis 49, 81 (1969); and 'Comprehensive Organic Transformations', Editor R. C. Larock, VCH 1989, page 685, or starting from the corresponding benzofuran- or dihydrobenzofuranaldehyde via reaction with ethylmagnesium chloride or ethylmagnesium bromide, for example analogously to 'Advanced Organic Chemistry', Editor J. March, McGraw-Hill Book Company, New York, 1985, page 816 et seq. and 1057 et seq.

The starting phenols of the formula II (Equation 1) can be obtained for example as shown in Equation 9 from the corresponding methoxy- or benzyloxy-substituted derivatives of the formula II₁ and II₂, respectively, in which R, R₁ and W are as defined under formula I.

Equation 9

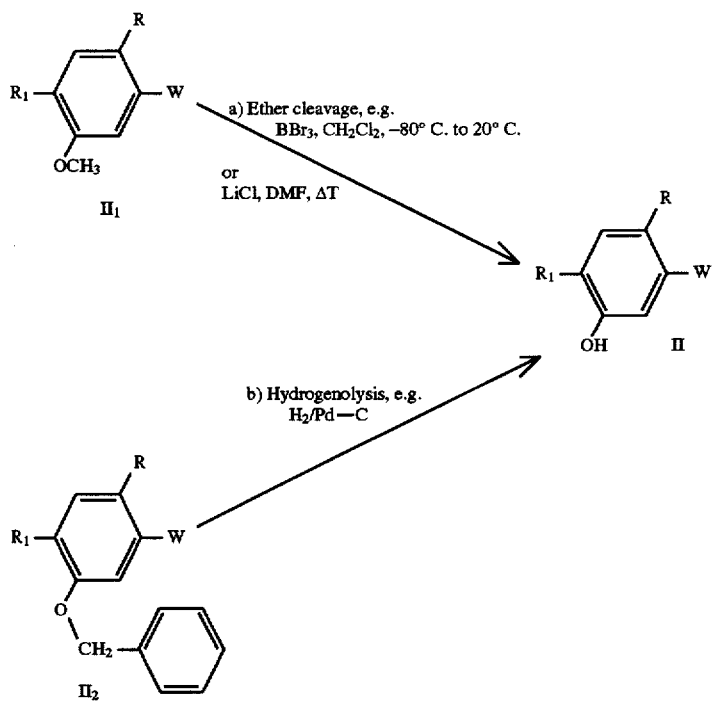

In accordance with Route a) of this equation, the compounds of the formula II₁ are subjected to ether cleavage by means of lithium chloride in N,N-dimethylformamide (DMF) at elevated temperature as described, for example, in Synthesis 1989, 287, or by means of boron tribromide in dichloromethane at temperatures of from −80° C. to 20° C. as described, for example, in Org. Synth., Collect. Vol. V, 412, 1973, or, in accordance with Route b), the compounds of the formula 112 are subjected to hydrogenolysis by means of hydrogen in the presence of a catalyst, for example palladium on charcoal, as described, for example, in J. Am. Chem. Soc. 93, 746 (1971).

The compounds of the formulae 114 and 112 in Equation 9 can be prepared by standard methods, for example as described in U.S. Pat. No. 4,452,981 and EP-A-0 061 741, from the known phenols of the formula II₃

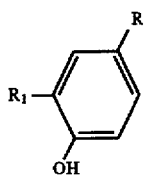

(II₃)

in which R and R₁ are as defined under formula I by nitrating the benzene ring, methylating or benzylating the phenol function and subsequently reducing the nitro group to give the corresponding aniline derivative of the formula II₄

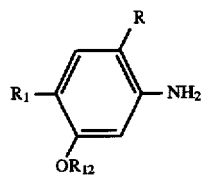

(II₄)

in which R and R₁ are as defined above and R₁₂ is methyl or benzyl and subsequently synthesizing the pyrazole rings W1 and W2 as described above.

The starting compounds of the formulae III, VI, IX, XIIa, XIIb, XIII and XVII in Equations 1, 4, 5 and 8 are known or can be prepared by processes which have been disclosed.

The intermediates of the formulae Va, Vb, VIII and X are novel. They are important intermediates for the synthesis of the compounds of the formula I. The invention therefore also relates to these compounds.

The preferences given for the compounds of the formula I equally apply to the intermediates of the formulae Va, Vb, VIII and X.

A large number of known standard processes, for example alkylation, halogenation, acylation, amidation, oximidation, oxidation and reduction, is suitable for the preparation of all other compounds of the formula I which are substituted in the 2-position of the benzofuranyl or dihydrobenzofuranyl ring (R₃), the choice of suitable preparation processes depending on the properties (reactivities) of the substituents in the intermediates in question.

The end products of the formula I can be isolated in the customary manner by concentration or by evaporating the solvent and purified by recrystallization or trituration of the solid residue in solvents in which they are sparingly soluble, such as ethers, aromatic hydrocarbons or chlorinated hydrocarbons, by distillation, or by means of column chromatography and a suitable eluent.

Those skilled in the art are familiar with the sequence in which certain reactions are to be carried out expediently, for example in Equations 1, 4, 5 and 6, to avoid any potential secondary reactions.

Unless a targeted synthesis is carried out to isolate pure isomers, the product may be obtained in the form of a mixture of two or more isomers. The isomers can be separated by methods known per se.

Application methods which are suitable for the use according to the invention of the compounds of the formula I or of compositions comprising them are all those which are conventionally used in agriculture, for example pre-emergence application, post-emergence application and seed dressing, and also a variety of methods and techniques, for example the controlled release of active ingredient. To this end, the dissolved active ingredient is applied to mineral granule carriers or polymerized granules (urea/formaldehyde) and the product is dried. If desired, an additional coating may be applied (coated granules), which allows the active ingredient to be released in a controlled manner over a specific period.

The compounds of the formula I can be employed in unaltered form, i.e. as obtained from the synthesis, but they are preferably processed in the customary manner together with the auxiliaries conventionally used in the art of formulation to give, for example, emulsifiable concentrates, directly sprayable or dilutable solutions, dilute emulsions, wettable powders, soluble powders, dusts, granules or microcapsules. The methods of application, such as spraying, atomizing, dusting, wetting, broadcasting or pouring, and also the type of composition are selected to suit intended aims and the prevailing circumstances.

The formulations, i.e. the compositions, preparations or products comprising the active ingredient of the formula I or at least one active ingredient of the formula I and, as a rule, one or more solid or liquid formulation auxiliaries are prepared in a known manner, for example intimately mixing and/or grinding the active ingredients with the formulation auxiliaries, for example solvents or solid carriers. Furthermore, surface-active compounds (surfactants) may additionally be used when preparing formulations.

The following solvents may be possible: aromatic hydrocarbons, preferably the fractions $C_8$ to $C_{12}$, for example xylene mixtures or substituted naphthalene, phthalic esters such as dibutyl phthalate or dioctyl phthalate, aliphatic hydrocarbons such as cyclohexane or paraffins, alcohols and glycols and their ethers and esters such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or N,N-dimethylformamide, and free or epoxidized vegetable oils such as epoxidized coconut oil or soya oil; or water.

Solid carriers which are used for example for dust and dispersible powders are, as a rule, ground natural minerals such as calcite, talc, kaolin, montmorillonite or attapulgite. To improve the physical properties of the formulation, it is also possible to add highly disperse silica or highly disperse absorptive polymers. Possible particulate, absorptive carriers for granules are porous types, for example pumice, brick grit, sepiolite or bentonite, and possible non-sorptive carrier materials are, for example, calcite or sand. In addition, a large number of pregranulated materials of inorganic or organic nature can be used such as, in particular, dolomite or comminuted plant residues.

Suitable surface-active compounds are, depending on the nature of the active ingredient of the formula I to be formulated, non-ionic, cationic and/or anionic surfactants and surfactant mixtures which have good emulsifying, dispersing and wetting properties.

Suitable anionic surfactants may be so-called water-soluble soaps, but also water-soluble synthetic surface-active compounds.

Soaps which may be mentioned are the alkali metal, alkaline earth metal or unsubstituted or substituted ammonium salts of higher fatty acids ($C_{10}$–$C_{22}$), for example the sodium or potassium salts of oleic or stearic acid, or of natural mixtures of fatty acids which can be obtained, for example, from coconut or tallow oil. The fatty acid methyltaurates may also be mentioned.

However, so-called synthetic surfactants are used more frequently, in particular fatty alcohol sulfonates, fatty alcohol sulfates, sulfonated benzimidazole derivatives or alkylarylsulfonates.

As a rule, the fatty alcohol sulfonates or fatty alcohol sulfates are in the form of alkali metal, alkaline earth metal or unsubstituted or substituted ammonium salts and have an alkyl radical with 8 to 22 carbon atoms, alkyl also including the alkyl moiety of acyl radicals, for example the sodium or calcium salt of ligninsulfonic acid, of the dodecylsulfuric ester or of a fatty alcohol sulfate mixture prepared from natural fatty acids. This section also includes the salts of the sulfuric esters and sulfonic acids of fatty alcohol/ethylene oxide adducts. The sulfonated benzimidazole derivatives have preferably 2 sulfonyl groups and a fatty acid radical with 8–22 carbon atoms. Examples of alkylarylsulfonates are the sodium, calcium or triethanolamine salts of the dodecylbenzenesulfonic acid, of dibutylnaphthalenesulfonic acid, or of a naphthalenesulfonic acid/formaldehyde condensate.

Suitable phosphates, for example salts of the phosphoric ester of a p-nonylphenol/(4–14)ethylene oxide adduct, or phospholipids, are furthermore also possible.

Non-ionic surfactants are mainly polyglycol ether derivatives of aliphatic or cycloaliphatic alcohols, of saturated or unsaturated fatty acids and of alkylphenols which can contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are water-soluble polethylene oxide adducts with polypropylene glycol, ethylene diaminopolypropylene glycol and alkyl polypropylene glycol which have 1 to 10 carbon atoms in the alkyl chain and 20 to 250 ethylene glycol ether groups and 10 to 100 propylene glycol ether groups. The abovementioned compounds normally contain 1 to 5 ethylene glycol units per propylene glycol unit.

Examples of non-ionic surfactants which may be mentioned are nonylphenolpolyethoxyethanols, castor oil polyglycol ethers, polypropylene polyethylene oxide adducts, tributylphenoxypolyethoxyethanol, polyethylene glycol and octylphenoxypolyethoxyethanol.

Other substances which are possible are fatty acid esters of polyoxyethylene sorbitan, such as polyoxyethylene sorbitan trioleate.

The cationic surfactants are mainly quaternary ammonium salts which have, as N-substituents, at least one alkyl radical with 8 to 22 carbon atoms and as further substituents lower, halogenated or unhalogenated alkyl, benzyl or lower hydroxyalkyl radicals. The salts are preferably in the form of halides, methylsulfates or ethylsulfates, for example stearyltrimethylammonium chloride or benzyldi(2-chloroethyl) ethylammonium bromide.

The surfactants conventionally used in the art of formulation, which can also be used in the compositions according to the invention, are described, inter alia, in "McCutcheon's Detergents and Emulsifiers Annual" MC Publishing Corp., Ridgewood, N.J., 1981, Stache, H., "Tensid-Taschenbuch" [Surfactants Guide], Carl Hanser Verlag, Munich/Vienna, 1981 and M. and J. Ash, "Encyclopedia of Surfactants", Vol I–III, Chemical Publishing Co., New York, 1980–81.

As a rule, the herbicidal formulations comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant.

While concentrated compositions are more preferred as commercially available goods, the end user uses, as a rule, dilute compositions.

The compositions can also comprise further additives such as stabilizers, for example free or epoxidized vegetable oils (epoxidized coconut oil, rapeseed oil or soya oil), antifoams, for example silicone oil, preservatives, viscosity regulators, binders, tackifiers and also fertilizers or other active ingredients.

Preferred formulations have, in particular, the following composition: (%=percent by weight)
Emulsifiable concentrates
 Active ingredient: 1 to 90%, preferably 5 to 50%
 Surfactant: 5 to 30%, preferably 10 to 20%
 Solvent: 15 to 94%, preferably 70 to 85%
Dusts
 Active ingredient: 0.1 to 50%, preferably 0.1 to 1%
 Solid carrier: 99.9 to 90%, preferably 99.9 to 99%
Suspension concentrates:
 Active ingredient: 5 to 75%, preferably 10 to 50%
 Water: 94 to 24% preferably 88 to 30%
 Surfactant: 1 to 40%, preferably 2 to 30%
Wettable powders:
 Active ingredient: 0.5 to 90%, preferably 1 to 80%
 Surfactant: 0.5 to 20%, preferably 1 to 15%
 Solid carrier: 5 to 95%, preferably 15 to 90%
Granules:
 Active ingredient: 0.1 to 30%, preferably 0.1 to 15%
 Solid carrier: 99.5 to 70%, preferably 97 to 85%

As a rule, the active ingredients of the formula I are applied successfully to the plant or its environment at a rate of application of from 0.001 to 4 kg/ha, in particular 0.005 to 2 kg/ha. The dosage required for the desired effect can be determined by experiments. It depends on the type of action, the development stage of the crop plant and of the weed, and on the application (location, timing, method) and may vary within wide ranges as a result of these parameters.

The compounds of the formula I are distinguished by herbicidal and growth-inhibiting properties which allow them to be used in crops of useful plants, in particular in cereals, cotton, soybeans, sugar beet, sugar cane, plantation crops, oilseed rape, maize and rice and for the non-selective control of weeds.

Crops are also to be understood as meaning those which have been made tolerant to herbicides or classes of herbicides by means of conventional breeding or by genetic engineering methods. The weeds to be controlled may be mono- and dicotylodonus weeds, for example Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, *Sorghum halepense*, Rottboellia, Cyperus, Abutilon, Sida, Xanthium, Amaranthus, Chenopodium, Ipomoea, Chrysanthemum, Galium, Viola and Veronica.

The Examples which follow illustrate the invention in greater detail without imposing any limitation.

PREPARATION EXAMPLES

Example H1

3-(4-Chloro-2-fluoro-5-(2'-chloroallyloxy)phenyl)-4-chloro-5-cyano-1-methyl-[1H]-pyrazole

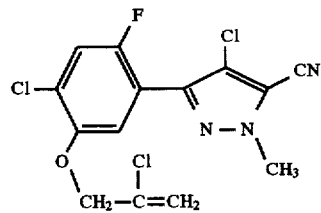

2.0 g (0.007 mol) of 3-(4-chloro-2-fluoro-5-hydroxyphenyl)-4-chloro-5-cyano-1-methyl-[1H]-pyrazole are dissolved in 20 ml of N-methylpyrrolidone (NMP). 2.90 g (3 equivalents) of anhydrous potassium carbonate are added with stirring and cooling in an ice-bath. 0.75 ml of 2,3-dichloropropane are then slowly added dropwise, and the mixture is stirred overnight at 50° C. The analytic thin-layer chromatogram of a worked-up sample shows that the reaction is complete. After the mixture has been cooled to 22° C., it is diluted with diethyl ether and washed first with ice-water and then with saline. The mixture is dried over sodium sulfate, filtered, and the filtrate is concentrated together with 5 g of silica gel. After the absorbate had been applied to a flash silica-gel column, elution takes place using n-hexane/ ethyl acetate 4/1. After the relevant fractions have been concentrated, 1.91 g of the desired product are obtained as a white solid (76% of theory).

Example H2
3-(4-Chloro-2-fluoro-5-hydroxy-6-allylphenyl)-4-chloro-5-cyano-1-methyl-[1H]-pyrazole

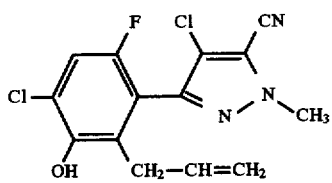

4.0 g (0.0123 mol) of 3-(4-chloro-2-fluoro-5-allyloxyphenyl)-4-chloro-5-cyano-1-methyl-[1H]-pyrazole are weighed into a flask and, with the condenser attached, first melted and then heated in an oil-bath at 195° C. After 3 hours, analysis by means of a thin-layer chromatogram shows that all starting material has reacted. The mixture is cooled to 22° C., and the residue is taken up in dichloromethane and applied to silica gel. The latter is applied to a flash silica-gel column. The column is first washed with n-hexane/ethyl acetate 5/1 and 1% of triethylamine and then eluted using carbon tetrachloride/ethyl acetate 5/1. After the eluate has been concentrated, the residue is partitioned between diethyl ether and water, the mixture is extracted by shaking and the phases are separated. The ether phase is washed with saline, dried over sodium sulfate and filtered, the filtrate is concentrated. This gives 2.83 g of the desired product as a pink solid (85% of theory) of m.p. 109°–110° C.

The following may also be obtained analogously to Example H2

Example H3
3-(4-Chloro-2-fluoro-5-hydroxy-6-(2'-chloroallyl)phenyl)-4-chloro-5-cyano-1 -methyl-[1H]-pyrazole,

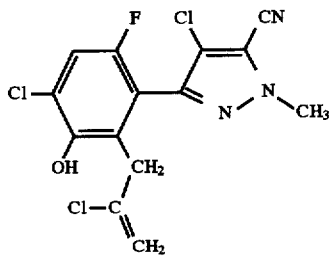

resin; yield 82% of theory.

Example H4

3-(4-Chloro-2-fluoro-5-hydroxy-6-but-2-ethylphenyl)-4-chloro-5-cyano-1-methyl -[1H]-pyrazole

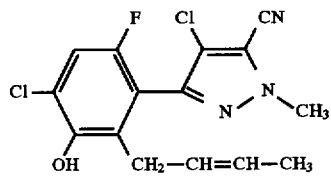

In a flask with attached condenser, 100 mg o f 3-(4-chloro-2-fluoro-5-methallyloxyphenyl)-4-chloro-5-cyano-1-methyl-[1H]-pyrazole are first melted and then heated for 3 hours in an oil-bath at 195° C. The melt is then cooled to 22° C. and taken up in dichloromethane. The dichloromethane solution is concentrated together with silica gel. After the silica gel has been applied to a flash silica-gel column, elution takes place with n-hexane/ethyl acetate 5/1. After the relevant fraction has been concentrated, 0.07 g of the desired product is obtained in the form of a resin (70% of theory).

Example H5

4-Chloro-3-(7-chloro-5-fluoro-2-hydroxymethyl-2,3-dihydrobenzofuran-4-yl)-1-methyl-[1H]-pyrazole-5-carbonitrile

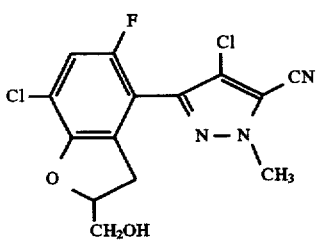

2.16 g (0.0066 mol) of 3-(4-chloro-2-fluoro-5-hydroxy-6-allylphenyl)-4-chloro-5-cyano -1-methyl-[1H]-pyrazole (Example H2) are introduced into 60 ml of chloroform. 2.29 g (1.1 equivalents) of meta-chloroperbenzoic acid (MCPA) are then added. The mixture is refluxed with stirring for 3 hours. A further 0.21 g (0.1 equivalent) of MCPA is then added. After the mixture has been refluxed for 2 hours it is diluted with diethyl ether and washed with aqueous sodium hydrogen carbonate solution and then washed with saline. After the mixture has been dried over sodium sulfate, it is filtered and concentrated. 2.98 g of crude product are obtained as a yellow resin. The crude product is applied to silica gel using dichloromethane, then applied to a flash silica-gel column and subsequently eluted with n-hexane/ ethyl 1/1 to 1/2. This give 2.07 g of the desired product in the form of a pale yellow resin (86% of theory).

Example H6
7-Chloro-4-(4-chloro-5-cyano-1-methyl-[1H]-pyrazol-3-yl)-5-fluoro-2,3-dihydrobenzofuran-2-ylmethyl acetate

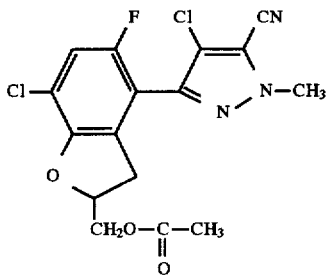

0.66 g (0.00193 mol) of 4-chloro-3-(7-chloro-5-fluoro-2-hydroxymethyl-2,3-dihydrobenzofuran-4-yl)-1-methyl-[1H]-pyrazole-5-carbonitrile (Example H5) is dissolved in 10 ml of pyridine. 0.20 ml of acetic anhydride (1.1 equivalents) is added with stirring and ice-cooling. The mixture is stirred for 30 minutes with ice-bath cooling and then for 6 hours at 22° C. The mixture is then poured into dilute hydrochloric acid and extracted with diethyl ether. The organic phase is washed with saline, dried over sodium sulfate and filtered, and the filtrate is applied to silica gel. After this has been applied to a flash silica-gel column, elution is carried out with n-hexane/ethyl acetate 5/1 to 2/1. This gives 0.50 g of the desired product as a colourless oil (67% of theory).

Example H7
4-Chloro-3-(7-chloro-5-fluoro-2-carboxyl-2,3-dihydrobenzofuran-4-yl)-1-methyl-[1H]-pyrazole-5-carbonitrile

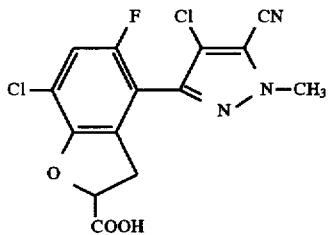

3 ml of a solution of Jones reagent (0.59 g of chromium trioxide, 0.53 ml of concentrated sulfuric acid, 3 ml of water) are added, with stirring and cooling in an ice-bath, to 2.07 g of 4-chloro-3-(7-chloro-5-fluoro-2-hydroxymethyl-2,3-dihydrobenzofuran-4-yl)-1 -methyl-[1H]-pyrazole-5-carbonitrile (Example H5) in 20 ml of acetone. The mixture is first stirred at temperatures below 5° C. and then for 12 hours at 22° C. Then, another 3 ml of the above Jones reagent are added, and the mixture is stirred for 9 hours at 22° C. The mixture is treated with water and then with diethyl ether and extracted by shaking, and the phases are separated. The ether phase is extracted with 1M sodium hydroxide solution. After the sodium hydroxide solution has been acidified with hydrochloric acid to pH 1, it is extracted with ethyl acetate, the organic phase is washed with saline, dried over sodium sulfate and filtered, and the filtrate is concentrated. The crude product is obtained as a brown resin in a yield of 1.0 g. The crude product is purified over a flash silica-gel column with a mixture of ethyl acetate/ethanol/acetic acid in a ratio of 95/5/1. This gives 0.51 g of the desired product as a solid (37% of theory).

Example H8
4-Chloro-3-(7-chloro-5-fluoro-2-methyl-2,3-dihydrobenzofuran-4-yl)-1-methyl-[1H]-pyrazole-5-carbonitrile

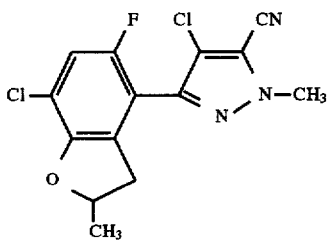

0.38 g of p-toluenesulfonic acid (0.81 equivalents) is introduced into 30 ml of xylene. The mixture is made absolute with stirring and refluxing on a water separator. The water separator is then removed, and 0.80 g (0.00245 mol) of 3-(4-chloro-2-fluoro-5-hydroxy-6-allylphenyl)-4-chloro-5-cyano-1-methyl-[1H]-pyrazole (Example H2) is added. The mixture is refluxed for 24 hours on a water separator. It is then cooled to 22° C., and the solvent is removed in vacuo. The residue is partitioned between diethyl ether and dilute aqueous sodium hydrogen carbonate solution. After the mixture has been extracted by shaking and the phases have been separated, the organic phase is washed with saline, dried over sodium sulfate and filtered, and the filtrate is applied to silica gel and this is applied to a flash silica-gel column. Elution is carried out with a gradient of n-hexane/ethyl acetate 5/1 to 1/1. The fractions which have an Rf value of 0.33 (relative to Rf=0.041 of the starting material; silica gel 60 $F_{254}$; n-hexane/ethyl acetate 5/2) are collected. 0.32 g of a colourless resin is obtained as crude product. Further purification by means of RP-HPLC (C18; 25×4 cm; acetonitrile/water 90/1 to 100/0; flow rate 30 ml/min) yields 0.06 g of a yellow resin (7.5% of theory).

Other compounds which can be prepared analogously are those listed in the Tables which follow.

TABLE 1

Compounds of the formula Ij

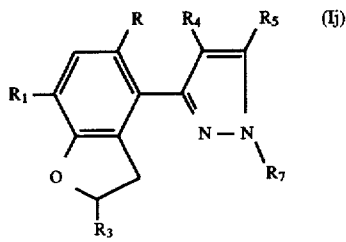

| Comp. No. | R | $R_1$ | $R_3$ | $R_4$ | $R_5$ | $R_7$ | Physical data |
|---|---|---|---|---|---|---|---|
| 1.1 | H | Cl | $CH_3$ | Cl | CN | $CH_3$ | |
| 1.2 | H | Cl | $CH_3$ | Cl | CN | $C_2H_5$ | |
| 1.3 | H | Cl | $CH_3$ | Cl | $CSNH_2$ | $CH_3$ | |
| 1.4 | H | Cl | $CH_3$ | Cl | $CSNH_2$ | $C_2H_5$ | |
| 1.5 | H | Cl | $CH_2Cl$ | Cl | CN | $CH_3$ | |
| 1.6 | H | Cl | $CH_2Br$ | Cl | CN | $CH_3$ | |
| 1.7 | H | Cl | $C_2H_5$ | Cl | CN | $CH_3$ | |
| 1.8 | H | Cl | $C_2H_5$ | Cl | CN | $C_2H_5$ | |
| 1.9 | H | Cl | $CH_2OH$ | Cl | CN | $CH_3$ | |
| 1.10 | H | Cl | $CH_2OCH_3$ | Cl | CN | $CH_3$ | |
| 1.11 | H | Cl | $CH_2OC_2H_5$ | Cl | CN | $CH_3$ | |
| 1.12 | H | Cl | $CH_2OCH_2OCH_3$ | Cl | CN | $CH_3$ | |
| 1.13 | H | Cl | $CH_2CN$ | Cl | CN | $CH_3$ | |
| 1.14 | H | Cl | $CH_2OCOCH_3$ | Cl | CN | $CH_3$ | |
| 1.15 | H | Cl | $CH_2OCOC_2H_5$ | Cl | CN | $CH_3$ | |
| 1.16 | H | Cl | COOH | Cl | CN | $CH_3$ | |
| 1.17 | H | Cl | $COOCH_3$ | Cl | CN | $CH_3$ | |
| 1.18 | H | Cl | $COOC_2H_5$ | Cl | CN | $CH_3$ | |
| 1.19 | H | Cl | $COOCH_2CH=CH_2$ | Cl | CN | $CH_3$ | |
| 1.20 | H | Cl | $COOCH_2C\equiv CH$ | Cl | CN | $CH_3$ | |
| 1.21 | H | Cl | $CONH_2$ | Cl | CN | $CH_3$ | |
| 1.22 | H | Cl | $CON(CH_3)_2$ | Cl | CN | $CH_3$ | |
| 1.23 | Cl | Cl | $CH_3$ | Cl | CN | $CH_3$ | |
| 1.24 | Cl | Cl | $CH_3$ | Cl | CN | $C_2H_5$ | |
| 1.25 | Cl | Cl | $CH_3$ | Cl | $CSNH_2$ | $CH_3$ | |
| 1.26 | Cl | Cl | $CH_3$ | Cl | $CSNH_2$ | $C_2H_5$ | |
| 1.27 | Cl | Cl | $CH_2Cl$ | Cl | CN | $CH_3$ | |
| 1.28 | Cl | Cl | $CH_2Cl$ | Cl | CN | $C_2H_5$ | |
| 1.29 | Cl | Cl | $CH_2Br$ | Cl | CN | $CH_3$ | |
| 1.30 | Cl | Cl | $C_2H_5$ | Cl | CN | $CH_3$ | |
| 1.31 | Cl | Cl | $C_2H_5$ | Cl | CN | $C_2H_5$ | |
| 1.32 | Cl | Cl | $CH_2OH$ | Cl | CN | $CH_3$ | |
| 1.33 | Cl | Cl | $CH_2OCH_3$ | Cl | CN | $CH_3$ | |
| 1.34 | Cl | Cl | $CH_2OCH_2OCH_3$ | Cl | CN | $CH_3$ | |
| 1.35 | Cl | Cl | $CH_2CN$ | Cl | CN | $CH_3$ | |
| 1.36 | Cl | Cl | $CH_2OCOCH_3$ | Cl | CN | $CH_3$ | |
| 1.37 | Cl | Cl | $CH_2OCOCH_2Cl$ | Cl | CN | $CH_3$ | |
| 1.38 | Cl | Cl | COOH | Cl | CN | $CH_3$ | |
| 1.39 | Cl | Cl | $COOCH_3$ | Cl | CN | $CH_3$ | |
| 1.40 | Cl | Cl | $COOC_2H_5$ | Cl | CN | $CH_3$ | |
| 1.41 | Cl | Cl | $COOCH(CH_3)_2$ | Cl | CN | $CH_3$ | |
| 1.42 | Cl | Cl | $COOCH_2CH_2Cl$ | Cl | CN | $CH_3$ | |
| 1.43 | Cl | Cl | $COOC_4H_9(n)$ | Cl | CN | $CH_3$ | |
| 1.44 | Cl | Cl | $COOCH_2CH=CH_2$ | Cl | CN | $CH_3$ | |
| 1.45 | Cl | Cl | $COOCH_2C\equiv CH$ | Cl | CN | $CH_3$ | |
| 1.46 | Cl | Cl | COO—cyclohexyl | Cl | CN | $CH_3$ | |
| 1.47 | Cl | Cl | $CONH_2$ | Cl | CN | $CH_3$ | |
| 1.48 | Cl | Cl | $CONHCH_3$ | Cl | CN | $CH_3$ | |
| 1.49 | Cl | Cl | $CON(CH_3)_2$ | Cl | CN | $CH_3$ | |
| 1.50 | Cl | Cl | $COOCH_2CH_2OCH_3$ | Cl | CN | $CH_3$ | |

TABLE 1-continued

Compounds of the formula Ij

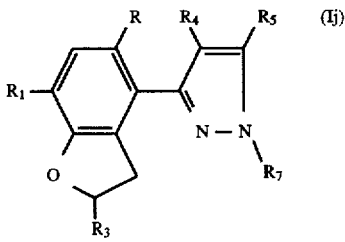

| Comp. No. | R | $R_1$ | $R_3$ | $R_4$ | $R_5$ | $R_7$ | Physical data |
|---|---|---|---|---|---|---|---|
| 1.51 | Cl | Cl | COOCH$_2$-C$_6$H$_5$ | Cl | CN | CH$_3$ | |
| 1.52 | Cl | Cl | CONHSO$_2$CH$_3$ | Cl | CN | CH$_3$ | |
| 1.53 | Cl | Cl | CH=NOCH$_3$ | Cl | CN | CH$_3$ | |
| 1.54 | Cl | Cl | CSNH$_2$ | Cl | CN | CH$_3$ | |
| 1.55 | Cl | Cl | CHO | Cl | CN | CH$_3$ | |
| 1.56 | Cl | Cl | CN | Cl | CN | CH$_3$ | |
| 1.57 | Cl | Cl | COOCH$_3$ | Cl | CN | C$_2$H$_5$ | |
| 1.58 | Cl | Cl | COOCH(CH$_3$)$_2$ | Cl | CN | C$_2$H$_5$ | |
| 1.59 | F | Cl | CH$_3$ | Cl | CN | CH$_3$ | Resin |
| 1.60 | F | Cl | CH$_3$ | Cl | CN | C$_2$H$_5$ | |
| 1.61 | F | Cl | CH$_3$ | Cl | CSNH$_2$ | CH$_3$ | |
| 1.62 | F | Cl | CH$_3$ | Cl | CSNH$_2$ | C$_2$H$_5$ | |
| 1.63 | F | Cl | CH$_2$Cl | Cl | CN | CH$_3$ | |
| 1.64 | F | Cl | CH$_2$Cl | Cl | CN | C$_2$H$_5$ | |
| 1.65 | F | Cl | CH$_2$Br | Cl | CN | CH$_3$ | |
| 1.66 | F | Cl | C$_2$H$_5$ | Cl | CN | CH$_3$ | |
| 1.67 | F | Cl | C$_2$H$_5$ | Cl | CN | C$_2$H$_5$ | |
| 1.68 | F | Cl | CH$_2$OH | Cl | CN | CH$_3$ | Resin |
| 1.69 | F | Cl | CH$_2$OH | Cl | CN | C$_2$H$_5$ | |
| 1.70 | F | Cl | CH$_2$OCH$_3$ | Cl | CN | CH$_3$ | |
| 1.71 | F | Cl | CH$_2$OCH$_3$ | Cl | CN | C$_2$H$_5$ | |
| 1.72 | F | Cl | CH$_2$OC$_2$H$_5$OCH$_3$ | Cl | CN | CH$_3$ | |
| 1.73 | F | Cl | CH$_2$CN | Cl | CN | CH$_3$ | |
| 1.74 | F | Cl | CH$_2$OCOCH$_3$ | Cl | CN | CH$_3$ | Resin |
| 1.75 | F | Cl | CH$_2$OCOCH$_2$Cl | Cl | CN | CH$_3$ | |
| 1.76 | F | Cl | COOH | Cl | CN | CH$_3$ | Resin |
| 1.77 | F | Cl | COOCH$_3$ | Cl | CN | CH$_3$ | Liquid |
| 1.78 | F | Cl | COOC$_2$H$_5$ | Cl | CN | CH$_3$ | Liquid |
| 1.79 | F | Cl | COOC$_3$H$_7$(n) | Cl | CN | CH$_3$ | |
| 1.80 | F | Cl | COOCH(CH$_3$)$_2$ | Cl | CN | CH$_3$ | Liquid |
| 1.81 | F | Cl | COOC$_4$H$_9$(n) | Cl | CN | CH$_3$ | |
| 1.82 | F | Cl | COOCH$_2$CH(CH$_3$)$_2$ | Cl | CN | CH$_3$ | |
| 1.83 | F | Cl | COOCH(CH$_3$)C$_2$H$_5$ | Cl | CN | CH$_3$ | |
| 1.84 | F | Cl | COOC$_5$H$_{11}$(n) | Cl | CN | CH$_3$ | |
| 1.85 | F | Cl | COOCH$_2$CH=CH$_2$ | Cl | CN | CH$_3$ | |
| 1.86 | F | Cl | COOCH$_2$C≡CH | Cl | CN | CH$_3$ | |
| 1.87 | F | Cl | COO-C$_6$H$_{11}$ | Cl | CN | CH$_3$ | |
| 1.88 | F | Cl | COOCH$_2$-C$_6$H$_5$ | Cl | CN | CH$_3$ | |
| 1.89 | F | Cl | COOCH$_3$ | Cl | CSNH$_2$ | CH$_3$ | |
| 1.90 | F | Cl | COOCH(CH$_3$)$_2$ | Cl | CSNH$_2$ | CH$_3$ | |
| 1.91 | F | Cl | CSNH$_2$ | Cl | CN | CH$_3$ | |
| 1.92 | F | Cl | CONHSO$_2$CH$_3$ | Cl | CN | CH$_3$ | |
| 1.93 | F | Cl | CH=NOCH$_3$ | Cl | CN | CH$_3$ | |
| 1.94 | F | Cl | CSNH$_2$ | Cl | CN | CH$_3$ | |
| 1.95 | F | Cl | CHO | Cl | CN | CH$_3$ | |
| 1.96 | F | Cl | CN | Cl | CN | CH$_3$ | |
| 1.97 | F | F | CH$_3$ | Cl | CN | CH$_3$ | |

TABLE 1-continued

Compounds of the formula Ij

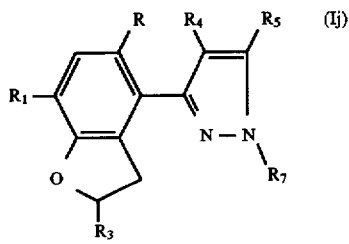

| Comp. No. | R | $R_1$ | $R_3$ | $R_4$ | $R_5$ | $R_7$ | Physical data |
|---|---|---|---|---|---|---|---|
| 1.98 | F | F | $CH_2Cl$ | Cl | CN | $CH_3$ | |
| 1.99 | F | F | $CH_2OH$ | Cl | CN | $CH_3$ | |
| 1.100 | F | F | COOH | Cl | CN | $CH_3$ | |
| 1.101 | F | F | $COOCH_3$ | Cl | CN | $CH_3$ | |
| 1.102 | F | F | $COOC_2H_5$ | Cl | CN | $CH_3$ | |
| 1.103 | F | F | $CH_2OCOCH_3$ | Cl | CN | $CH_3$ | |
| 1.104 | F | F | CHO | Cl | CN | $CH_3$ | |
| 1.105 | F | F | CN | Cl | CN | $CH_3$ | |
| 1.106 | F | CN | $CH_3$ | Cl | CN | $CH_3$ | |
| 1.107 | F | CN | $CH_2OH$ | Cl | CN | $CH_3$ | |
| 1.108 | F | CN | $COOCH_3$ | Cl | CN | $CH_3$ | |
| 1.109 | F | CN | $COOCH(CH_3)_2$ | Cl | CN | $CH_3$ | |
| 1.110 | H | Cl | $CH_3$ | Cl | CN | H | |
| 1.111 | H | Cl | $COOCH_3$ | Cl | CN | H | |
| 1.112 | Cl | Cl | $CH_3$ | Cl | CN | H | |
| 1.113 | F | Cl | $CH_3$ | Cl | CN | H | |
| 1.114 | F | Cl | $CH_3$ | Cl | CN | H | |
| 1.115 | F | Cl | $COOCH_3$ | Cl | CN | H | |
| 1.116 | F | Cl | $CH_2OH$ | Cl | CN | H | |
| 1.117 | F | Cl | $CH_2Cl$ | Cl | CN | H | |
| 1.118 | F | Cl | $COOCH(CH_3)_2$ | Cl | CN | H | |
| 1.119 | F | Br | $CH_3$ | Cl | CN | $CH_3$ | |

TABLE 2

Compounds of the formula Ik

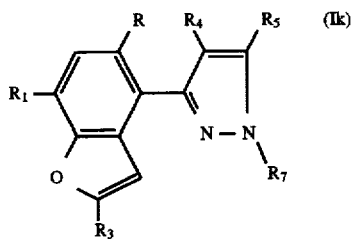

| Comp. No. | R | $R_1$ | $R_3$ | $R_4$ | $R_5$ | $R_7$ | Physical data |
|---|---|---|---|---|---|---|---|
| 2.1 | H | Cl | $CH_3$ | Cl | CN | $CH_3$ | |
| 2.2 | H | Cl | $CH_3$ | Cl | CN | $C_2H_5$ | |
| 2.3 | H | Cl | $CH_3$ | Cl | $CSNH_2$ | $CH_3$ | |
| 2.4 | H | Cl | $CH_3$ | Cl | $CSNH_2$ | $C_2H_5$ | |
| 2.5 | H | Cl | $CH_2Cl$ | Cl | CN | $CH_3$ | |
| 2.6 | H | Cl | $CH_2Br$ | Cl | CN | $CH_3$ | |
| 2.7 | H | Cl | $C_2H_5$ | Cl | CN | $CH_3$ | |
| 2.8 | H | Cl | $C_2H_5$ | Cl | CN | $C_2H_5$ | |
| 2.9 | H | Cl | $CH_2OH$ | Cl | CN | $CH_3$ | |
| 2.10 | H | Cl | $CH_2OCH_3$ | Cl | CN | $CH_3$ | |
| 2.11 | H | Cl | $CH_2OC_2H_5$ | Cl | CN | $CH_3$ | |
| 2.12 | H | Cl | $CH_2OCH_2OCH_3$ | Cl | CN | $CH_3$ | |
| 2.13 | H | Cl | $CH_2CN$ | Cl | CN | $CH_3$ | |
| 2.14 | H | Cl | $CH_2OCOCH_3$ | Cl | CN | $CH_3$ | |
| 2.15 | H | Cl | $CH_2OCOC_2H_5$ | Cl | CN | $CH_3$ | |
| 2.16 | H | Cl | COOH | Cl | CN | $CH_3$ | |
| 2.17 | H | Cl | $COOCH_3$ | Cl | CN | $CH_3$ | |
| 2.18 | H | Cl | $COOC_2H_5$ | Cl | CN | $CH_3$ | |

TABLE 2-continued

Compounds of the formula Ik

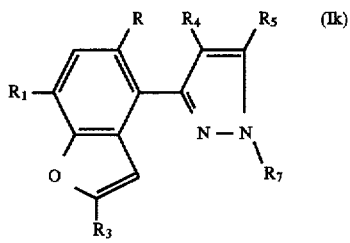

| Comp. No. | R | $R_1$ | $R_3$ | $R_4$ | $R_5$ | $R_7$ | Physical data |
|---|---|---|---|---|---|---|---|
| 2.19 | H | Cl | $COOCH_2CH=CH_2$ | Cl | CN | $CH_3$ | |
| 2.20 | H | Cl | $COOCH_2C\equiv CH$ | Cl | CN | $CH_3$ | |
| 2.21 | H | Cl | $CONH_2$ | Cl | CN | $CH_3$ | |
| 2.22 | H | Cl | $CON(CH_3)_2$ | Cl | CN | $CH_3$ | |
| 2.23 | Cl | Cl | $CH_3$ | Cl | CN | $CH_3$ | |
| 2.24 | Cl | Cl | $CH_3$ | Cl | CN | $C_2H_5$ | |
| 2.25 | Cl | Cl | $CH_3$ | Cl | $CSNH_2$ | $CH_3$ | |
| 2.26 | Cl | Cl | $CH_3$ | Cl | $CSNH_2$ | $C_2H_5$ | |
| 2.27 | Cl | Cl | $CH_2Cl$ | Cl | CN | $CH_3$ | |
| 2.28 | Cl | Cl | $CH_2Cl$ | Cl | CN | $C_2H_5$ | |
| 2.29 | Cl | Cl | $CH_2Br$ | Cl | CN | $CH_3$ | |
| 2.30 | Cl | Cl | $C_2H_5$ | Cl | CN | $CH_3$ | |
| 2.31 | Cl | Cl | $C_2H_5$ | Cl | CN | $C_2H_5$ | |
| 2.32 | Cl | Cl | $CH_2OH$ | Cl | CN | $CH_3$ | |
| 2.33 | Cl | Cl | $CH_2OCH_3$ | Cl | CN | $CH_3$ | |
| 2.34 | Cl | Cl | $CH_2OCH_2OCH_3$ | Cl | CN | $CH_3$ | |
| 2.35 | Cl | Cl | $CH_2CN$ | Cl | CN | $CH_3$ | |
| 2.36 | Cl | Cl | $CH_2OCOCH_3$ | Cl | CN | $CH_3$ | |
| 2.37 | Cl | Cl | $CH_2OCOCH_2Cl$ | Cl | CN | $CH_3$ | |
| 2.38 | Cl | Cl | COOH | Cl | CN | $CH_3$ | |
| 2.39 | Cl | Cl | $COOCH_3$ | Cl | CN | $CH_3$ | |
| 2.40 | Cl | Cl | $COOC_2H_5$ | Cl | CN | $CH_3$ | |
| 2.41 | Cl | Cl | $COOCH(CH_3)_2$ | Cl | CN | $CH_3$ | |
| 2.42 | Cl | Cl | $COOCH_2CH_2Cl$ | Cl | CN | $CH_3$ | |
| 2.43 | Cl | Cl | $COOC_4H_9(n)$ | Cl | CN | $CH_3$ | |
| 2.44 | Cl | Cl | $COOCH_2CH=CH_2$ | Cl | CN | $CH_3$ | |
| 2.45 | Cl | Cl | $COOCH_2C\equiv CH$ | Cl | CN | $CH_3$ | |
| 2.46 | Cl | Cl | COO—(cyclohexyl) | Cl | CN | $CH_3$ | |
| 2.47 | Cl | Cl | $CONH_2$ | Cl | CN | $CH_3$ | |
| 2.48 | Cl | Cl | $CONHCH_3$ | Cl | CN | $CH_3$ | |
| 2.49 | Cl | Cl | $CON(CH_3)_2$ | Cl | CN | $CH_3$ | |
| 2.50 | Cl | Cl | $COOCH_2CH_2OCH_3$ | Cl | CN | $CH_3$ | |
| 2.51 | Cl | Cl | $COOCH_2$—(phenyl) | Cl | CN | $CH_3$ | |
| 2.52 | Cl | Cl | $CONHSO_2CH_3$ | Cl | CN | $CH_3$ | |
| 2.53 | Cl | Cl | $CH=NOCH_3$ | Cl | CN | $CH_3$ | |
| 2.54 | Cl | Cl | $CSNH_2$ | Cl | CN | $CH_3$ | |
| 2.55 | Cl | Cl | CHO | Cl | CN | $CH_3$ | |
| 2.56 | Cl | Cl | CN | Cl | CN | $CH_3$ | |
| 2.57 | Cl | Cl | $COOCH_3$ | Cl | CN | $C_2H_5$ | |
| 2.58 | Cl | Cl | $COOCH(CH_3)_2$ | Cl | CN | $C_2H_5$ | |
| 2.59 | F | Cl | $CH_3$ | Cl | CN | $CH_3$ | |
| 2.60 | F | Cl | $CH_3$ | Cl | CN | $C_2H_5$ | |
| 2.61 | F | Cl | $CH_3$ | Cl | $CSNH_2$ | $CH_3$ | |
| 2.62 | F | Cl | $CH_3$ | Cl | $CSNH_2$ | $C_2H_5$ | |
| 2.63 | F | Cl | $CH_2Cl$ | Cl | CN | $CH_3$ | |
| 2.64 | F | Cl | $CH_2Cl$ | Cl | CN | $C_2H_5$ | |
| 2.65 | F | Cl | $CH_2Br$ | Cl | CN | $CH_3$ | |
| 2.66 | F | Cl | $C_2H_5$ | Cl | CN | $CH_3$ | |
| 2.67 | F | Cl | $C_2H_5$ | Cl | CN | $C_2H_5$ | |

TABLE 2-continued

Compounds of the formula Ik

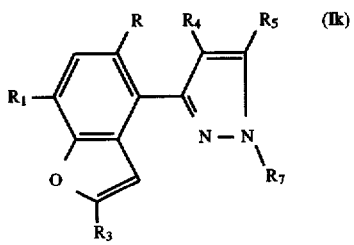

| Comp. No. | R | $R_1$ | $R_3$ | $R_4$ | $R_5$ | $R_7$ | Physical data |
|---|---|---|---|---|---|---|---|
| 2.68 | F | Cl | $CH_2OH$ | Cl | CN | $CH_3$ | |
| 2.69 | F | Cl | $CH_2OH$ | Cl | CN | $C_2H_5$ | |
| 2.70 | F | Cl | $CH_2OCH_3$ | Cl | CN | $CH_3$ | |
| 2.71 | F | Cl | $CH_2OCH_3$ | Cl | CN | $C_2H_5$ | |
| 2.72 | F | Cl | $CH_2OC_2H_5OCH_3$ | Cl | CN | $CH_3$ | |
| 2.73 | F | Cl | $CH_2CN$ | Cl | CN | $CH_3$ | |
| 2.74 | F | Cl | $CH_2OCOCH_3$ | Cl | CN | $CH_3$ | |
| 2.75 | F | Cl | $CH_2OCOCH_2Cl$ | Cl | CN | $CH_3$ | |
| 2.76 | F | Cl | COOH | Cl | CN | $CH_3$ | |
| 2.77 | F | Cl | $COOCH_3$ | Cl | CN | $CH_3$ | |
| 2.78 | F | Cl | $COOC_2H_5$ | Cl | CN | $CH_3$ | |
| 2.79 | F | Cl | $COOC_3H_7(n)$ | Cl | CN | $CH_3$ | |
| 2.80 | F | Cl | $COOCH(CH_3)_2$ | Cl | CN | $CH_3$ | |
| 2.81 | F | Cl | $COOC_4H_9(n)$ | Cl | CN | $CH_3$ | |
| 2.82 | F | Cl | $COOCH_2CH(CH_3)_2$ | Cl | CN | $CH_3$ | |
| 2.83 | F | Cl | $COOCH(CH_3)C_2H_5$ | Cl | CN | $CH_3$ | |
| 2.84 | F | Cl | $COOC_5H_{11}(n)$ | Cl | CN | $CH_3$ | |
| 2.85 | F | Cl | $COOCH_2CH=CH_2$ | Cl | CN | $CH_3$ | |
| 2.86 | F | Cl | $COOCH_2C\equiv CH$ | Cl | CN | $CH_3$ | |
| 2.87 | F | Cl | COO-cyclohexyl | Cl | CN | $CH_3$ | |
| 2.88 | F | Cl | $COOCH_2$-phenyl | Cl | CN | $CH_3$ | |
| 2.89 | F | Cl | $COOCH_3$ | Cl | $CSNH_2$ | $CH_3$ | |
| 2.90 | F | Cl | $COOCH(CH_3)_2$ | Cl | $CSNH_2$ | $CH_3$ | |
| 2.91 | F | Cl | $CSNH_2$ | Cl | CN | $CH_3$ | |
| 2.92 | F | Cl | $CONHSO_2CH_3$ | Cl | CN | $CH_3$ | |
| 2.93 | F | Cl | $CH=NOCH_3$ | Cl | CN | $CH_3$ | |
| 2.94 | F | Cl | $CSNH_2$ | Cl | CN | $CH_3$ | |
| 2.95 | F | Cl | CHO | Cl | CN | $CH_3$ | |
| 2.96 | F | Cl | CN | Cl | CN | $CH_3$ | |
| 2.97 | F | F | $CH_3$ | Cl | CN | $CH_3$ | |
| 2.98 | F | F | $CH_2Cl$ | Cl | CN | $CH_3$ | |
| 2.99 | F | F | $CH_2OH$ | Cl | CN | $CH_3$ | |
| 2.100 | F | F | COOH | Cl | CN | $CH_3$ | |
| 2.101 | F | F | $COOCH_3$ | Cl | CN | $CH_3$ | |
| 2.102 | F | F | $COOC_2H_5$ | Cl | CN | $CH_3$ | |
| 2.103 | F | F | $CH_2OCOCH_3$ | Cl | CN | $CH_3$ | |
| 2.104 | F | F | CHO | Cl | CN | $CH_3$ | |
| 2.105 | F | F | CN | Cl | CN | $CH_3$ | |
| 2.106 | F | CN | $CH_3$ | Cl | CN | $CH_3$ | |
| 2.107 | F | CN | $CH_2OH$ | Cl | CN | $CH_3$ | |
| 2.108 | F | CN | $COOCH_3$ | Cl | CN | $CH_3$ | |
| 2.109 | F | CN | $COOCH(CH_3)_2$ | Cl | CN | $CH_3$ | |
| 2.110 | H | Cl | $CH_3$ | Cl | CN | H | |
| 2.111 | H | Cl | $COOCH_3$ | Cl | CN | H | |
| 2.112 | Cl | Cl | $CH_3$ | Cl | CN | H | |
| 2.113 | F | Cl | $CH_3$ | Cl | CN | H | |
| 2.114 | F | Cl | $CH_3$ | Cl | CN | H | |
| 2.115 | F | Cl | $COOCH_3$ | Cl | CN | H | |
| 2.116 | F | Cl | $CH_2OH$ | Cl | CN | H | |
| 2.117 | F | Cl | $CH_2Cl$ | Cl | CN | H | |

TABLE 2-continued

Compounds of the formula Ik

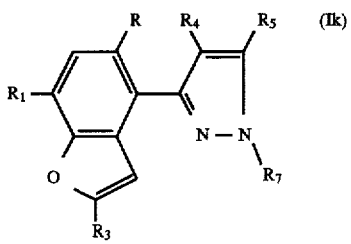

| Comp. No. | R | $R_1$ | $R_3$ | $R_4$ | $R_5$ | $R_7$ | Physical data |
|---|---|---|---|---|---|---|---|
| 2.118 | F | Cl | COOCH(CH$_3$)$_2$ | Cl | CN | H | |
| 2.119 | F | Br | CH$_3$ | Cl | CN | CH$_3$ | |

TABLE 3

Compounds of the formula Im

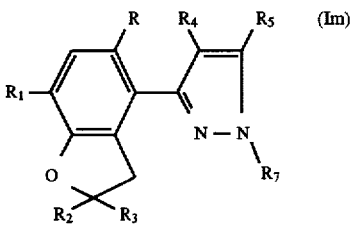

| Comp. No. | R | $R_1$ | $R_2$ | $R_3$ | $R_4$ | $R_5$ | $R_7$ | Physical data |
|---|---|---|---|---|---|---|---|---|
| 3.1 | H | Cl | CH$_3$ | CH$_3$ | Cl | CN | H | |
| 3.2 | H | Cl | CH$_3$ | C$_2$H$_5$ | Cl | CN | H | |
| 3.3 | H | Cl | CH$_3$ | CH$_2$OH | Cl | CN | H | |
| 3.4 | H | Cl | CH$_3$ | CH$_2$Cl | Cl | CN | H | |
| 3.5 | H | Cl | CH$_3$ | CH$_2$OCOCH$_3$ | Cl | CN | H | |
| 3.6 | H | Cl | CH$_3$ | CH$_3$ | Cl | CN | CH$_3$ | |
| 3.7 | H | Cl | CH$_3$ | CH$_3$ | Cl | CN | C$_2$H$_5$ | |
| 3.8 | H | Cl | CH$_3$ | CH$_3$ | Cl | CSNH$_2$ | CH$_3$ | |
| 3.9 | H | Cl | CH$_3$ | CH$_3$ | Cl | CSNH$_2$ | C$_2$H$_5$ | |
| 3.10 | H | Cl | CH$_3$ | CH$_2$OH | Cl | CN | CH$_3$ | |
| 3.11 | H | Cl | CH$_3$ | CH$_2$Cl | Cl | CN | CH$_3$ | |
| 3.12 | H | Cl | CH$_3$ | CH$_2$Br | Cl | CN | CH$_3$ | |
| 3.13 | H | Cl | CH$_3$ | CH$_2$OCH$_3$ | Cl | CN | CH$_3$ | |
| 3.14 | H | Cl | CH$_3$ | CH$_2$OC$_2$H$_5$ | Cl | CN | CH$_3$ | |
| 3.15 | H | Cl | CH$_3$ | CH$_2$CN | Cl | CN | CH$_3$ | |
| 3.16 | H | Cl | CH$_3$ | CH$_2$OCOCH$_3$ | Cl | CN | CH$_3$ | |
| 3.17 | H | Cl | CH$_3$ | CH$_2$OCOCH$_2$Cl | Cl | CN | CH$_3$ | |
| 3.18 | H | Cl | CH$_3$ | CH$_2$OCOC$_2$H$_5$ | Cl | CN | CH$_3$ | |
| 3.19 | H | Cl | CH$_3$ | COOH | Cl | CN | CH$_3$ | |
| 3.20 | H | Cl | CH$_3$ | COOCH$_3$ | Cl | CN | CH$_3$ | |
| 3.21 | H | Cl | CH$_3$ | COOCH$_3$ | Cl | CSNH$_2$ | CH$_3$ | |
| 3.22 | H | Cl | CH$_3$ | COOCH(CH$_3$)$_2$ | Cl | CN | CH$_3$ | |
| 3.23 | H | Cl | CH$_3$ | COOCH$_2$CH=CH$_2$ | Cl | CN | CH$_3$ | |
| 3.24 | H | Cl | CH$_3$ | COOCH$_2$C≡CH | Cl | CN | CH$_3$ | |
| 3.25 | H | Cl | CH$_3$ | COONH$_2$ | Cl | CN | CH$_3$ | |
| 3.26 | H | Cl | CH$_3$ | COONHCH$_3$ | Cl | CN | CH$_3$ | |
| 3.27 | Cl | Cl | CH$_3$ | CH$_3$ | Cl | CN | CH$_3$ | |
| 3.28 | Cl | Cl | CH$_3$ | C$_2$H$_5$ | Cl | CN | CH$_3$ | |
| 3.29 | Cl | Cl | CH$_3$ | CH$_2$OH | Cl | CN | CH$_3$ | |
| 3.30 | Cl | Cl | CH$_3$ | CH$_3$ | Cl | CSNH$_2$ | CH$_3$ | |
| 3.31 | Cl | Cl | CH$_3$ | CH$_2$Cl | Cl | CN | CH$_3$ | |
| 3.32 | Cl | Cl | CH$_3$ | CH$_2$Br | Cl | CN | CH$_3$ | |
| 3.33 | Cl | Cl | CH$_3$ | CH$_2$OCH$_3$ | Cl | CN | CH$_3$ | |
| 3.34 | Cl | Cl | CH$_3$ | CH$_2$CN | Cl | CN | CH$_3$ | |
| 3.35 | Cl | Cl | CH$_3$ | CH$_2$OCOCH$_3$ | Cl | CN | CH$_3$ | |
| 3.36 | Cl | Cl | CH$_3$ | CH$_2$OCOCH$_2$Cl | Cl | CN | CH$_3$ | |
| 3.37 | Cl | Cl | CH$_3$ | COOH | Cl | CN | CH$_3$ | |

TABLE 3-continued

Compounds of the formula Im

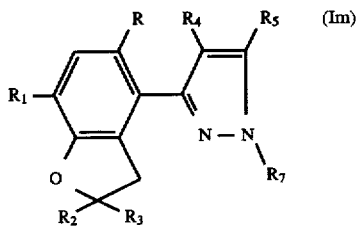

(Im)

| Comp. No. | R | $R_1$ | $R_2$ | $R_3$ | $R_4$ | $R_5$ | $R_7$ | Physical data |
|---|---|---|---|---|---|---|---|---|
| 3.38 | Cl | Cl | $CH_3$ | $COOCH_3$ | Cl | CN | $CH_3$ | |
| 3.39 | Cl | Cl | $CH_3$ | $COOC_2H_5$ | Cl | CN | $CH_3$ | |
| 3.40 | Cl | Cl | $CH_3$ | $COOCH_3$ | Cl | $CSNH_2$ | $CH_3$ | |
| 3.41 | Cl | Cl | $CH_3$ | $COOCH_3$ | Cl | CN | $C_2H_5$ | |
| 3.42 | Cl | Cl | $CH_3$ | $COOCH(CH_3)_2$ | Cl | CN | $CH_3$ | |
| 3.43 | Cl | Cl | $CH_3$ | $COOCH_2CH=CH_2$ | Cl | CN | $CH_3$ | |
| 3.44 | Cl | Cl | $CH_3$ | $COOCH_2C\equiv CH$ | Cl | CN | $CH_3$ | |
| 3.45 | Cl | Cl | $CH_3$ | $CONH_2$ | Cl | CN | $CH_3$ | |
| 3.46 | Cl | Cl | $CH_3$ | $CON(CH_3)_2$ | Cl | CN | $CH_3$ | |
| 3.47 | Cl | Cl | $CH_3$ | CN | Cl | CN | $CH_3$ | |
| 3.48 | Cl | Cl | $CH_3$ | CHO | Cl | CN | $CH_3$ | |
| 3.49 | Cl | Cl | $CH_3$ | CH=NOH | Cl | CN | $CH_3$ | |
| 3.50 | Cl | Cl | $CH_3$ | $CH=NOCH_3$ | Cl | CN | $CH_3$ | |
| 3.51 | Cl | Cl | $CH_3$ | $CH_3$ | Cl | CN | H | |
| 3.52 | Cl | Cl | $CH_3$ | $COOCH_3$ | Cl | CN | H | |
| 3.53 | F | Cl | $CH_3$ | $CH_3$ | Cl | CN | $CH_3$ | |
| 3.54 | F | Cl | $CH_3$ | $C_2H_5$ | Cl | CN | $CH_3$ | |
| 3.55 | F | Cl | $CH_3$ | $CH_2OH$ | Cl | CN | $CH_3$ | |
| 3.56 | F | Cl | $CH_3$ | $CH_3$ | Cl | $CSNH_2$ | $CH_3$ | |
| 3.57 | F | Cl | $CH_3$ | $CH_2Cl$ | Cl | CN | $CH_3$ | |
| 3.58 | F | Cl | $CH_3$ | $CH_2Br$ | Cl | CN | $CH_3$ | |
| 3.59 | F | Cl | $CH_3$ | $CH_2OCH_3$ | Cl | CN | $CH_3$ | |
| 3.60 | F | Cl | $CH_3$ | $CH_2CN$ | Cl | CN | $CH_3$ | |
| 3.61 | F | Cl | $CH_3$ | $CH_2OCOCH_3$ | Cl | CN | $CH_3$ | |
| 3.62 | F | Cl | $CH_3$ | $CH_2OCOCH_2Cl$ | Cl | CN | $CH_3$ | |
| 3.63 | F | Cl | $CH_3$ | COOH | Cl | CN | $CH_3$ | |
| 3.64 | F | Cl | $CH_3$ | $COOCH_3$ | Cl | CN | $CH_3$ | |
| 3.65 | F | Cl | $CH_3$ | $COOC_2H_5$ | Cl | CN | $CH_3$ | |
| 3.66 | F | Cl | $CH_3$ | $COOCH_3$ | Cl | $CSNH_2$ | $CH_3$ | |
| 3.67 | F | Cl | $CH_3$ | $COOCH_3$ | Cl | CN | $C_2H_5$ | |
| 3.68 | F | Cl | $CH_3$ | $COOC_2H_5$ | Cl | CN | $CH_3$ | |
| 3.69 | F | Cl | $CH_3$ | $COOC_3H_7(n)$ | Cl | CN | $CH_3$ | |
| 3.70 | F | Cl | $CH_3$ | $COOCH(CH_3)_2$ | Cl | CN | $CH_3$ | |
| 3.71 | F | Cl | $CH_3$ | $COOC_4H_9(n)$ | Cl | CN | $CH_3$ | |
| 3.72 | F | Cl | $CH_3$ | $COOCH_2CH(CH_3)_2$ | Cl | CN | $CH_3$ | |
| 3.73 | F | Cl | $CH_3$ | $COOCH(CH_3)C_2H_5$ | Cl | CN | $CH_3$ | |
| 3.74 | F | Cl | $CH_3$ | $COOC_5H_{11}(n)$ | Cl | CN | $CH_3$ | |
| 3.75 | F | Cl | $CH_3$ | $COOCH_2CH=CH_2$ | Cl | CN | $CH_3$ | |
| 3.76 | F | Cl | $CH_3$ | $COOCH_2C\equiv CH$ | Cl | CN | $CH_3$ | |
| 3.77 | F | Cl | $CH_3$ | COO—cyclohexyl | Cl | CN | $CH_3$ | |
| 3.78 | F | Cl | $CH_3$ | $COOCH_2$—phenyl | Cl | CN | $CH_3$ | |
| 3.79 | F | Cl | $CH_3$ | $COOCH_3$ | Cl | $CSNH_2$ | $CH_3$ | |
| 3.80 | F | Cl | $CH_3$ | $COOCH(CH_3)_2$ | Cl | $CSNH_2$ | $CH_3$ | |
| 3.81 | F | Cl | $CH_3$ | $CONHSO_2CH_3$ | Cl | CN | $CH_3$ | |
| 3.82 | F | Cl | $CH_3$ | $CH=NOCH_3$ | Cl | CN | $CH_3$ | |
| 3.83 | F | Cl | $CH_3$ | $CSNH_2$ | Cl | CN | $CH_3$ | |
| 3.84 | F | Cl | $CH_3$ | CHO | Cl | CN | $CH_3$ | |
| 3.85 | F | Cl | $CH_3$ | CN | Cl | CN | $CH_3$ | |
| 3.86 | F | F | $CH_3$ | $CH_2OH$ | Cl | CN | $CH_3$ | |
| 3.87 | F | F | $CH_3$ | $CH_2Cl$ | Cl | CN | $CH_3$ | |
| 3.88 | F | F | $CH_3$ | COOH | Cl | CN | $CH_3$ | |

TABLE 3-continued

Compounds of the formula Im

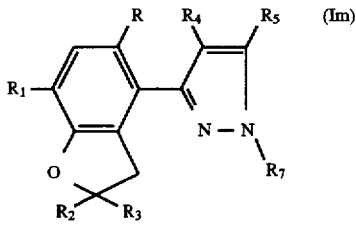

| Comp. No. | R | $R_1$ | $R_2$ | $R_3$ | $R_4$ | $R_5$ | $R_7$ | Physical data |
|---|---|---|---|---|---|---|---|---|
| 3.89 | F | F | $CH_3$ | $COOCH_3$ | Cl | CN | $CH_3$ | |
| 3.90 | F | F | $CH_3$ | $COOCH(CH_3)_2$ | Cl | CN | $CH_3$ | |
| 3.91 | F | CN | $CH_3$ | $CH_3$ | Cl | CN | $CH_3$ | |
| 3.92 | F | CN | $CH_3$ | $CH_2OH$ | Cl | CN | $CH_3$ | |
| 3.93 | F | CN | $CH_3$ | COOH | Cl | CN | $CH_3$ | |
| 3.94 | F | CN | $CH_3$ | $COOCH_3$ | Cl | CN | $CH_3$ | |
| 3.95 | F | CN | $CH_3$ | $COOCH(CH_3)_2$ | Cl | CN | $CH_3$ | |
| 3.96 | F | Br | $CH_3$ | $CH_3$ | Cl | CN | $CH_3$ | |
| 3.97 | F | Br | $CH_3$ | $CH_3$ | Cl | CN | $CH_3$ | |
| 3.98 | F | Br | $CH_3$ | $COOCH_3$ | Cl | CN | $CH_3$ | |
| 3.99 | F | Cl | $CH_3$ | $CH_2OH$ | Cl | CN | H | |
| 3.100 | F | Cl | $CH_3$ | $COOCH_3$ | Cl | CN | H | |

TABLE 4

Compounds of the formula In

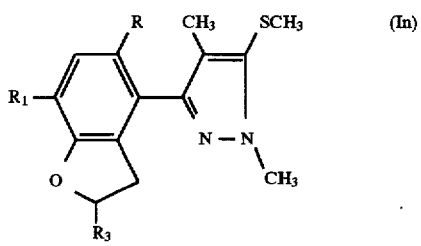

| Comp. No. | R | $R_1$ | $R_3$ | Physical data |
|---|---|---|---|---|
| 4.1 | H | Cl | $CH_3$ | |
| 4.2 | H | Cl | $CH_2OH$ | |
| 4.3 | H | Cl | $CH_2Cl$ | |
| 4.4 | H | Cl | $CH_2Br$ | |
| 4.5 | H | Cl | $CH_2OCH_3$ | |
| 4.6 | H | Cl | $CH_2CN$ | |
| 4.7 | H | Cl | $CH_2OC_2H_5$ | |
| 4.8 | H | Cl | COOH | |
| 4.9 | H | Cl | $COOCH_3$ | |
| 4.10 | H | Cl | $COOC_2H_5$ | |
| 4.11 | H | Cl | $COOCH(CH_3)_2$ | |
| 4.12 | H | Cl | $COOCH_2CH=CH_2$ | |
| 4.13 | H | Cl | $COOCH_2C\equiv CH$ | |
| 4.14 | H | Cl | $CONH_2$ | |
| 4.15 | H | Cl | $CONHCH_3$ | |
| 4.16 | H | Cl | $CSNH_2$ | |
| 4.17 | Cl | Cl | $CH_3$ | |
| 4.18 | Cl | Cl | $CH_2OH$ | |
| 4.19 | Cl | Cl | $CH_2Cl$ | |
| 4.20 | Cl | Cl | $CH_3$ | |
| 4.21 | Cl | Cl | $CH_2OH$ | |
| 4.22 | Cl | Cl | $CH_2Cl$ | |
| 4.23 | Cl | Cl | $CH_2Br$ | |
| 4.24 | Cl | Cl | $CH_2OCH_3$ | |
| 4.25 | Cl | Cl | COOH | |
| 4.26 | Cl | Cl | $COOCH_3$ | |
| 4.27 | Cl | Cl | $COOCH(CH_3)_2$ | |
| 4.28 | Cl | Cl | $COOCH_2CH=CH_2$ | |
| 4.29 | Cl | Cl | $CONH_2$ | |
| 4.30 | F | Cl | $CH_3$ | |
| 4.31 | F | Cl | $CH_2OH$ | |
| 4.32 | F | Cl | $CH_2Cl$ | |
| 4.33 | F | Cl | $CH_2Br$ | |
| 4.34 | F | Cl | $C_2H_5$ | |
| 4.35 | F | Cl | $CH_2OCH_3$ | |
| 4.36 | F | Cl | $CH_2OCOCH_3$ | |
| 4.37 | F | Cl | $CH_2OCOCH_2Cl$ | |
| 4.38 | F | Cl | COOH | |
| 4.39 | F | Cl | $COOCH_3$ | |
| 4.40 | F | Cl | $COOC_2H_5$ | |
| 4.41 | F | Cl | $COOC_3H_7(n)$ | |
| 4.42 | F | Cl | $COOCH(CH_3)_2$ | |
| 4.43 | F | Cl | $COOC_4H_9(n)$ | |
| 4.44 | F | Cl | $COOCH_2CH(CH_3)_2$ | |
| 4.45 | F | Cl | $COOCH(CH_3)C_2H_5$ | |
| 4.46 | F | Cl | $COOCH_2CH_2COOCH_3$ | |
| 4.47 | F | Cl | $COOCH_2CH=CH_2$ | |
| 4.48 | F | Cl | $COOCH_2C\equiv CH$ | |

TABLE 4-continued

Compounds of the formula In

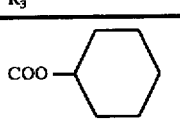

(In)

| Comp. No. | R | $R_1$ | $R_3$ | Physical data |
|---|---|---|---|---|
| 4.49 | F | Cl | COO-cyclohexyl | |
| 4.50 | F | Cl | COOCH$_2$-phenyl | |
| 4.51 | F | Cl | CN | |
| 4.52 | F | Cl | CSNH$_2$ | |
| 4.53 | F | Cl | CONH$_2$ | |
| 4.54 | F | Cl | CONHCH$_3$ | |
| 4.55 | F | Cl | CON(CH$_3$)$_2$ | |
| 4.56 | F | Cl | CH=NOH | |
| 4.57 | F | Cl | CH=NOCH$_3$ | |
| 4.58 | F | F | CH$_3$ | |
| 4.59 | F | F | CH$_2$Cl | |
| 4.60 | F | F | CH$_2$OH | |
| 4.61 | F | F | COOH | |
| 4.62 | F | F | COOCH$_3$ | |
| 4.63 | F | F | COOCH(CH$_3$)$_2$ | |
| 4.64 | F | F | CH$_2$COCH$_3$ | |
| 4.65 | F | Br | CH$_3$ | |
| 4.66 | F | Br | COOCH$_3$ | |
| 4.67 | F | Br | COOCH(CH$_3$)$_2$ | |
| 4.68 | F | CN | CH$_3$ | |
| 4.69 | F | CN | COOCH$_3$ | |
| 4.70 | F | CN | COOCH(CH$_3$)$_2$ | |
| 4.71 | F | CN | CHO | |
| 4.72 | F | CN | CONH$_2$ | |
| 4.73 | F | CN | CONHCH$_3$ | |

TABLE 5

Compounds of the formula Io

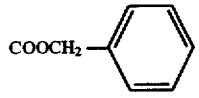

(Io)

| Comp. No. | R | $R_1$ | $R_3$ | Physical data |
|---|---|---|---|---|
| 5.1 | H | Cl | CH$_3$ | |
| 5.2 | H | Cl | CH$_2$OH | |
| 5.3 | H | Cl | CH$_2$Cl | |
| 5.4 | H | Cl | CH$_2$Br | |

TABLE 5-continued

Compounds of the formula Io

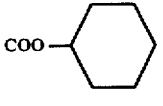

(Io)

| Comp. No. | R | $R_1$ | $R_3$ | Physical data |
|---|---|---|---|---|
| 5.5 | H | Cl | CH$_2$OCH$_3$ | |
| 5.6 | H | Cl | CH$_2$CN | |
| 5.7 | H | Cl | CH$_2$OC$_2$H$_5$ | |
| 5.8 | H | Cl | COOH | |
| 5.9 | H | Cl | COOCH$_3$ | |
| 5.10 | H | Cl | COOC$_2$H$_5$ | |
| 5.11 | H | Cl | COOCH(CH$_3$)$_2$ | |
| 5.12 | H | Cl | COOCH$_2$CH=CH$_2$ | |
| 5.13 | H | Cl | COOCH$_2$C=CH | |
| 5.14 | H | Cl | CONH$_2$ | |
| 5.15 | H | Cl | CONHCH$_3$ | |
| 5.16 | H | Cl | CSNH$_2$ | |
| 5.17 | Cl | Cl | CH$_3$ | |
| 5.18 | Cl | Cl | CH$_2$OH | |
| 5.19 | Cl | Cl | CH$_2$Cl | |
| 5.20 | Cl | Cl | CH$_3$ | |
| 5.21 | Cl | Cl | CH$_2$OH | |
| 5.22 | Cl | Cl | CH$_2$Cl | |
| 5.23 | Cl | Cl | CH$_2$Br | |
| 5.24 | Cl | Cl | CH$_2$OCH$_3$ | |
| 5.25 | Cl | Cl | COOH | |
| 5.26 | Cl | Cl | COOCH$_3$ | |
| 5.27 | Cl | Cl | COOCH(CH$_3$)$_2$ | |
| 5.28 | Cl | Cl | COOCH$_2$CH=CH$_2$ | |
| 5.29 | Cl | Cl | CONH$_2$ | |
| 5.30 | F | Cl | CH$_3$ | |
| 5.31 | F | Cl | CH$_2$OH | |
| 5.32 | F | Cl | CH$_2$Cl | |
| 5.33 | F | Cl | CH$_2$Br | |
| 5.34 | F | Cl | C$_2$H$_5$ | |
| 5.35 | F | Cl | CH$_2$OCH$_3$ | |
| 5.36 | F | Cl | CH$_2$OCOCH$_3$ | |
| 5.37 | F | Cl | CH$_2$OCOCH$_2$Cl | |
| 5.38 | F | Cl | COOH | |
| 5.39 | F | Cl | COOCH$_3$ | |
| 5.40 | F | Cl | COOC$_2$H$_5$ | |
| 5.41 | F | Cl | COOC$_3$H$_7$(n) | |
| 5.42 | F | Cl | COOCH(CH$_3$)$_2$ | |
| 5.43 | F | Cl | COOC$_4$H$_9$(n) | |
| 5.44 | F | Cl | COOCH$_2$CH(CH$_3$)$_2$ | |
| 5.45 | F | Cl | COOCH(CH$_3$)C$_2$H$_5$ | |
| 5.46 | F | Cl | COOCH$_2$CH$_2$CH$_2$COOCH$_3$ | |
| 5.47 | F | Cl | COOCH$_2$CH=CH$_2$ | |
| 5.48 | F | Cl | COOCH$_2$C=CH | |
| 5.49 | F | Cl | COO-cyclohexyl | |
| 5.50 | F | Cl | COOCH$_2$-phenyl | |
| 5.51 | F | Cl | CN | |
| 5.52 | F | Cl | CSNH$_2$ | |
| 5.53 | F | Cl | CONH$_2$ | |
| 5.54 | F | Cl | CONHCH$_3$ | |
| 5.55 | F | Cl | CON(CH$_3$)$_2$ | |

TABLE 5-continued

Compounds of the formula Io

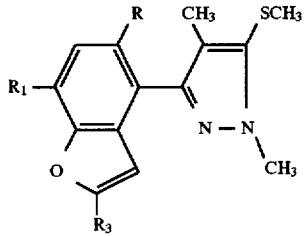

| Comp. No. | R | $R_1$ | $R_3$ | Physical data |
|---|---|---|---|---|
| 5.56 | F | Cl | CH=NOH | |
| 5.57 | F | Cl | CH=NOCH$_3$ | |
| 5.58 | F | F | CH$_3$ | |
| 5.59 | F | F | CH$_2$Cl | |
| 5.60 | F | F | CH$_2$OH | |
| 5.61 | F | F | COOH | |
| 5.62 | F | F | COOCH$_3$ | |
| 5.63 | F | F | COOCH(CH$_3$)$_2$ | |
| 5.84 | F | F | CH$_2$COCH$_3$ | |
| 5.65 | F | Br | CH$_3$ | |
| 5.66 | F | Br | COOCH$_3$ | |
| 5.67 | F | Br | COOCH(CH$_3$)$_2$ | |
| 5.68 | F | CN | CH$_3$ | |
| 5.69 | F | CN | COOCH$_3$ | |
| 5.70 | F | CN | COOCH(CH$_3$)$_2$ | |
| 5.71 | F | CN | CHO | |
| 5.72 | F | CN | CONH$_2$ | |
| 5.73 | F | CN | CONHCH$_3$ | |

TABLE 6

Compounds of the formula Ip

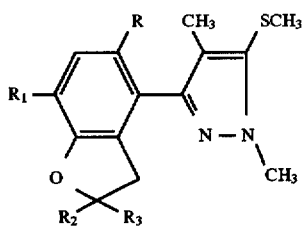

| Comp. No. | R | $R_1$ | $R_2$ | $R_3$ | Physical data |
|---|---|---|---|---|---|
| 6.16 | H | Cl | CH$_3$ | CH$_3$ | |
| 6.2 | H | Cl | CH$_3$ | C2H$_5$ | |
| 6.3 | H | Cl | CH$_3$ | CH$_2$OH | |
| 6.4 | H | Cl | CH$_3$ | CH$_2$Cl | |
| 6.5 | H | Cl | CH$_3$ | CH$_2$OCOCH$_3$ | |
| 6.6 | H | Cl | CH$_3$ | CH$_3$ | |
| 6.7 | H | Cl | CH$_3$ | CH$_3$ | |
| 6.8 | H | Cl | CH$_3$ | CH$_3$ | |
| 6.9 | H | Cl | CH$_3$ | CH$_3$ | |
| 6.10 | H | Cl | CH$_3$ | CH$_2$OH | |
| 6.11 | H | Cl | CH$_3$ | CH$_2$Cl | |
| 6.12 | H | Cl | CH$_3$ | CH$_2$Br | |
| 6.13 | H | Cl | CH$_3$ | CH$_2$OCH$_3$ | |
| 6.14 | H | Cl | CH$_3$ | CH$_2$OC$_2$H$_5$ | |
| 6.15 | H | Cl | CH$_3$ | CH$_2$CN | |
| 6.16 | H | Cl | CH$_3$ | CH$_2$OCOCH$_3$ | |
| 6.17 | H | Cl | CH$_3$ | CH$_2$OCOCH$_2$Cl | |
| 6.18 | H | Cl | CH$_3$ | CH$_2$OCOC$_2$H$_5$ | |
| 6.19 | H | Cl | CH$_3$ | COOH | |
| 6.20 | H | Cl | CH$_3$ | COOCH$_3$ | |

TABLE 6-continued

Compounds of the formula Ip

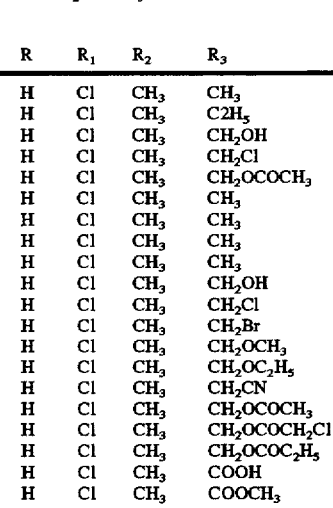

| Comp. No. | R | $R_1$ | $R_2$ | $R_3$ | Physical data |
|---|---|---|---|---|---|
| 6.21 | H | Cl | CH$_3$ | COOCH$_3$ | |
| 6.22 | H | Cl | CH$_3$ | COOCH(CH$_3$)$_2$ | |
| 6.23 | H | Cl | CH$_3$ | COOCH$_2$CH=CH$_2$ | |
| 6.24 | H | Cl | CH$_3$ | COOCH$_2$C=CH | |
| 6.25 | H | Cl | CH$_3$ | COONH$_2$ | |
| 6.26 | H | Cl | CH$_3$ | COONHCH$_3$ | |
| 6.27 | Cl | Cl | CH$_3$ | CH$_3$ | |
| 6.28 | Cl | Cl | CH$_3$ | C$_2$H$_5$ | |
| 6.29 | Cl | Cl | CH$_3$ | CH$_2$OH | |
| 6.30 | Cl | Cl | CH$_3$ | CH$_3$ | |
| 6.31 | Cl | Cl | CH$_3$ | CH$_2$Cl | |
| 6.32 | Cl | Cl | CH$_3$ | CH$_2$Br | |
| 6.33 | Cl | Cl | CH$_3$ | CH$_2$OCH$_3$ | |
| 6.34 | Cl | Cl | CH$_3$ | CH$_2$CN | |
| 6.35 | Cl | Cl | CH$_3$ | CH$_2$OCOCH$_3$ | |
| 6.36 | Cl | Cl | CH$_3$ | CH$_2$OCOCH$_2$Cl | |
| 6.37 | Cl | Cl | CH$_3$ | COOH | |
| 6.38 | Cl | Cl | CH$_3$ | COOCH$_3$ | |
| 6.39 | Cl | Cl | CH$_3$ | COOC$_2$H$_5$ | |
| 6.40 | Cl | Cl | CH$_3$ | COOCH$_3$ | |
| 6.41 | Cl | Cl | CH$_3$ | COOCH$_3$ | |
| 6.42 | Cl | Cl | CH$_3$ | COOCH(CH$_3$)$_2$ | |
| 6.43 | Cl | Cl | CH$_3$ | COOCH$_2$CH=CH$_2$ | |
| 6.44 | Cl | Cl | CH$_3$ | COOCH$_2$C=CH | |
| 6.45 | Cl | Cl | CH$_3$ | CONH$_2$ | |
| 6.46 | Cl | Cl | CH$_3$ | CON(CH$_3$)$_2$ | |
| 6.47 | Cl | Cl | CH$_3$ | CN | |
| 6.48 | Cl | Cl | CH$_3$ | CHO | |
| 6.49 | Cl | Cl | CH$_3$ | CH=NOH | |
| 6.50 | Cl | Cl | CH$_3$ | CH=NOCH$_3$ | |
| 6.51 | Cl | Cl | CH$_3$ | CH$_3$ | |
| 6.52 | Cl | Cl | CH$_3$ | COOCH$_3$ | |
| 6.53 | F | Cl | CH$_3$ | CH$_3$ | |
| 6.54 | F | Cl | CH$_3$ | C2H$_5$ | |
| 6.55 | F | Cl | CH$_3$ | CH$_2$OH | |
| 6.56 | F | Cl | CH$_3$ | CH$_3$ | |
| 6.57 | F | Cl | CH$_3$ | CH$_2$Cl | |
| 6.58 | F | Cl | CH$_3$ | CH$_2$Br | |
| 6.59 | F | Cl | CH$_3$ | CH$_2$OCH$_3$ | |
| 6.60 | F | Cl | CH$_3$ | CH$_2$CN | |
| 6.61 | F | Cl | CH$_3$ | CH$_2$OCOCH$_3$ | |
| 6.62 | F | Cl | CH$_3$ | CH$_2$OCOCH$_2$Cl | |
| 6.63 | F | Cl | CH$_3$ | COOH | |
| 6.64 | F | Cl | CH$_3$ | COOCH$_3$ | |
| 6.65 | F | Cl | CH$_3$ | COOC$_2$H$_5$ | |
| 6.66 | F | Cl | CH$_3$ | COOCH$_3$ | |
| 6.67 | F | Cl | CH$_3$ | COOCH$_3$ | |
| 6.68 | F | Cl | CH$_3$ | COOC$_2$H$_5$ | |
| 6.69 | F | Cl | CH$_3$ | COOC$_3$H$_7$(n) | |
| 6.70 | F | Cl | CH$_3$ | COOCH(CH$_3$)$_2$ | |
| 6.71 | F | Cl | CH$_3$ | COOC$_4$H$_9$(n) | |
| 6.72 | F | Cl | CH$_3$ | COOCH$_2$CH(CH$_3$)$_2$ | |
| 6.73 | F | Cl | CH$_3$ | COOCH(CH$_3$)C$_2$H$_5$ | |
| 6.74 | F | Cl | CH$_3$ | COOC$_5$H$_{11}$(n) | |
| 6.75 | F | Cl | CH$_3$ | COOCH$_2$CH=CH$_2$ | |
| 6.76 | F | Cl | CH$_3$ | COOCH$_2$C=CH | |
| 6.77 | F | Cl | CH$_3$ | COO—⟨cyclohexyl⟩ | |

TABLE 6-continued

Compounds of the formula Ip

| Comp. No. | R | R₁ | R₂ | R₃ | Physical data |
|---|---|---|---|---|---|
| 6.78 | F | Cl | $CH_3$ | COOCH₂—C₆H₅ | |
| 6.79 | F | Cl | $CH_3$ | $COOCH_3$ | |
| 6.80 | F | Cl | $CH_3$ | $COOCH(CH_3)_2$ | |
| 6.81 | F | Cl | $CH_3$ | $CONHSO_2CH_3$ | |
| 6.82 | F | Cl | $CH_3$ | $CH=NOCH_3$ | |
| 6.83 | F | Cl | $CH_3$ | $CSNH_2$ | |
| 6.84 | F | Cl | $CH_3$ | CHO | |
| 6.85 | F | Cl | $CH_3$ | CN | |
| 6.86 | F | F | $CH_3$ | $CH_2OH$ | |
| 6.87 | F | F | $CH_3$ | $CH_2Cl$ | |
| 6.88 | F | F | $CH_3$ | COOH | |
| 6.89 | F | F | $CH_3$ | $COOCH_3$ | |
| 6.90 | F | F | $CH_3$ | $COOCH(CH_3)_2$ | |
| 6.91 | F | CN | $CH_3$ | $CH_3$ | |
| 6.92 | F | CN | $CH_3$ | $CH_2OH$ | |
| 6.93 | F | CN | $CH_3$ | COOH | |
| 6.94 | F | CN | $CH_3$ | $COOCH_3$ | |
| 6.95 | F | CN | $CH_3$ | $COOCH(CH_3)_2$ | |
| 6.96 | F | Br | $CH_3$ | $CH_3$ | |
| 6.97 | F | Br | $CH_3$ | $CH_3$ | |
| 6.98 | F | Br | $CH_3$ | $COOCH_3$ | |
| 6.99 | F | Cl | $CH_3$ | $CH_2OH$ | |
| 6.100 | F | Cl | $CH_3$ | $COOCH_3$ | |

TABLE 7

Compounds of the formula Iq

| Comp. No. | R | R₁ | R₃ | Physical data |
|---|---|---|---|---|
| 7.1 | H | Cl | $CH_3$ | |
| 7.2 | H | Cl | $CH_2OH$ | |
| 7.3 | H | Cl | $CH_2Cl$ | |
| 7.4 | H | Cl | $CH_2Br$ | |
| 7.5 | H | Cl | $CH_2OCH_3$ | |
| 7.6 | H | Cl | $CH_2CN$ | |
| 7.7 | H | Cl | $CH_2OC_2H_5$ | |
| 7.8 | H | Cl | COOH | |
| 7.9 | H | Cl | $COOCH_3$ | |
| 7.10 | H | Cl | $COOC_2H_5$ | |
| 7.11 | H | Cl | $COOCH(CH_3)_2$ | |
| 7.12 | H | Cl | $COOCH_2CH=CH_2$ | |
| 7.13 | H | Cl | $COOCH_2C\equiv CH$ | |
| 7.14 | H | Cl | $CONH_2$ | |
| 7.15 | H | Cl | $CONHCH_3$ | |
| 7.16 | H | Cl | $CSNH_2$ | |
| 7.17 | Cl | Cl | $CH_3$ | |
| 7.18 | Cl | Cl | $CH_2OH$ | |
| 7.19 | Cl | Cl | $CH_2Cl$ | |
| 7.20 | Cl | Cl | $CH_3$ | |
| 7.21 | Cl | Cl | $CH_2OH$ | |
| 7.22 | Cl | Cl | $CH_2Cl$ | |
| 7.23 | Cl | Cl | $CH_2Br$ | |
| 7.24 | Cl | Cl | $CH_2OCH_3$ | |
| 7.25 | Cl | Cl | COOH | |
| 7.26 | Cl | Cl | $COOCH_3$ | |
| 7.27 | Cl | Cl | $COOCH(CH_3)_2$ | |
| 7.28 | Cl | Cl | $COOCH_2CH=CH_2$ | |
| 7.29 | Cl | Cl | $CONH_2$ | |
| 7.30 | F | Cl | $CH_3$ | |
| 7.31 | F | Cl | $CH_2OH$ | |
| 7.32 | F | Cl | $CH_2Cl$ | |
| 7.33 | F | Cl | $CH_2Br$ | |
| 7.34 | F | Cl | $C_2H_5$ | |
| 7.35 | F | Cl | $CH_2OCH_3$ | |
| 7.36 | F | Cl | $CH_2OCOCH_3$ | |
| 7.37 | F | Cl | $CH_2OCOCH_2Cl$ | |
| 7.38 | F | Cl | COOH | |
| 7.39 | F | Cl | $COOCH_3$ | |
| 7.40 | F | Cl | $COOC_2H_5$ | |
| 7.41 | F | Cl | $COOC_3H_7(n)$ | |
| 7.42 | F | Cl | $COOCH(CH_3)_2$ | |
| 7.43 | F | Cl | $COOC_4H_9(n)$ | |
| 7.44 | F | Cl | $COOCH_2CH(CH_3)_2$ | |
| 7.45 | F | Cl | $COOCH(CH_3)C_2H_5$ | |
| 7.46 | F | Cl | $COOCH_2CH_2CH_2COOCH_3$ | |
| 7.47 | F | Cl | $COOCH_2CH=CH_2$ | |
| 7.48 | F | Cl | $COOCH_2C\equiv CH$ | |
| 7.49 | F | Cl | COO—C₆H₁₁ | |
| 7.50 | F | Cl | COOCH₂—C₆H₅ | |
| 7.51 | F | Cl | CN | |
| 7.52 | F | Cl | $CSNH_2$ | |
| 7.53 | F | Cl | $CONH_2$ | |
| 7.54 | F | Cl | $CONHCH_3$ | |
| 7.55 | F | Cl | $CON(CH_3)_2$ | |
| 7.56 | F | Cl | CH=NOH | |
| 7.57 | F | Cl | $CH=NOCH_3$ | |
| 7.58 | F | F | $CH_3$ | |
| 7.59 | F | F | $CH_2Cl$ | |
| 7.60 | F | F | $CH_2OH$ | |
| 7.61 | F | F | COOH | |

TABLE 7-continued

Compounds of the formula Iq

Structure (Iq): benzofuran-based compound with substituents R, R₁, R₃, CH₃, SOCH₃, and N—N(CH₃) group.

| Comp. No. | R | R₁ | R₃ | Physical data |
|---|---|---|---|---|
| 7.62 | F | F | COOCH₃ | |
| 7.63 | F | F | COOCH(CH₃)₂ | |
| 7.64 | F | F | CH₂COCH₃ | |
| 7.65 | F | Br | CH₃ | |
| 7.66 | F | Br | COOCH₃ | |
| 7.67 | F | Br | COOCH(CH₃)₂ | |
| 7.68 | F | CN | CH₃ | |
| 7.69 | F | CN | COOCH₃ | |
| 7.70 | F | CN | COOCH(CH₃)₂ | |
| 7.71 | F | CN | CHO | |
| 7.72 | F | CN | CONH₂ | |
| 7.73 | F | CN | CONHCH₃ | |

TABLE 8

Compounds of the formula Ir

Structure (Ir): benzofuran-based compound with substituents R, R₁, R₃, CH₃, SOCH₃, and N—N(CH₃) group.

| Comp. No. | R | R₁ | R₃ | Physical data |
|---|---|---|---|---|
| 8.1 | H | Cl | CH₃ | |
| 8.2 | H | Cl | CH₂OH | |
| 8.3 | H | Cl | CH₂Cl | |
| 8.4 | H | Cl | CH₂Br | |
| 8.5 | H | Cl | CH₂OCH₃ | |
| 8.6 | H | Cl | CH₂CN | |
| 8.7 | H | Cl | CH₂OC₂H₅ | |
| 8.8 | H | Cl | COOH | |
| 8.9 | H | Cl | COOCH₃ | |
| 8.10 | H | Cl | COOC₂H₅ | |
| 8.11 | H | Cl | COOCH(CH₃)₂ | |
| 8.12 | H | Cl | COOCH₂CH=CH₂ | |
| 8.13 | H | Cl | COOCH₂C≡CH | |
| 8.14 | H | Cl | CONH₂ | |
| 8.15 | H | Cl | CONHCH₃ | |
| 8.16 | H | Cl | CSNH₂ | |
| 8.17 | Cl | Cl | CH₃ | |
| 8.18 | Cl | Cl | CH₂OH | |
| 8.19 | Cl | Cl | CH₂Cl | |
| 8.20 | Cl | Cl | CH₃ | |
| 8.21 | Cl | Cl | CH₂OH | |
| 8.22 | Cl | Cl | CH₂Cl | |
| 8.23 | Cl | Cl | CH₂Br | |
| 8.24 | Cl | Cl | CH₂OCH₃ | |
| 8.25 | Cl | Cl | COOH | |
| 8.26 | Cl | Cl | COOCH₃ | |
| 8.27 | Cl | Cl | COOCH(CH₃)₂ | |
| 8.28 | Cl | Cl | COOCH₂CH=CH₂ | |
| 8.29 | Cl | Cl | CONH₂ | |
| 8.30 | F | Cl | CH₃ | |
| 8.31 | F | Cl | CH₂OH | |
| 8.32 | F | Cl | CH₂Cl | |
| 8.33 | F | Cl | CH₂Br | |
| 8.34 | F | Cl | C₂H₅ | |
| 8.35 | F | Cl | CH₂OCH₃ | |
| 8.36 | F | Cl | CH₂OCOCH₃ | |
| 8.37 | F | Cl | CH₂OCOCH₂Cl | |
| 8.38 | F | Cl | COOH | |
| 8.39 | F | Cl | COOCH₃ | |
| 8.40 | F | Cl | COOC₂H₅ | |
| 8.41 | F | Cl | COOC₃H₇(n) | |
| 8.42 | F | Cl | COOCH(CH₃)₂ | |
| 8.43 | F | Cl | COOC₄H₉(n) | |
| 8.44 | F | Cl | COOCH₂CH(CH₃)₂ | |
| 8.45 | F | Cl | COOCH(CH₃)C₂H₅ | |
| 8.46 | F | Cl | COOCH₂CH₂CH₂COOCH₃ | |
| 8.47 | F | Cl | COOCH₂CH=CH₂ | |
| 8.48 | F | Cl | COOCH₂C≡CH | |
| 8.49 | F | Cl | COO—cyclohexyl | |
| 8.50 | F | Cl | COOCH₂—phenyl | |
| 8.51 | F | Cl | CN | |
| 8.52 | F | Cl | CSNH₂ | |
| 8.53 | F | Cl | CONH₂ | |
| 8.54 | F | Cl | CONHCH₃ | |
| 8.55 | F | Cl | CON(CH₃)₂ | |
| 8.56 | F | Cl | CH=NOH | |
| 8.57 | F | Cl | CH=NOCH₃ | |
| 8.58 | F | F | CH₃ | |
| 8.59 | F | F | CH₂Cl | |
| 8.60 | F | F | CH₂OH | |
| 8.61 | F | F | COOH | |
| 8.62 | F | F | COOCH₃ | |
| 8.63 | F | F | COOCH(CH₃)₂ | |
| 8.64 | F | F | CH₂COCH₃ | |
| 8.65 | F | Br | CH₃ | |
| 8.66 | F | Br | COOCH₃ | |
| 8.67 | F | Br | COOCH(CH₃)₂ | |
| 8.68 | F | CN | CH₃ | |
| 8.69 | F | CN | COOCH₃ | |
| 8.70 | F | CN | COOCH(CH₃)₂ | |
| 8.71 | F | CN | CHO | |
| 8.72 | F | CN | CONH₂ | |
| 8.73 | F | CN | CONHCH₃ | |

TABLE 9

Compounds of the formula Is $$\text{(Is)}$$

| Comp. No. | R | $R_1$ | $R_2$ | $R_3$ | Physical data |
|---|---|---|---|---|---|
| 9.1 | H | Cl | $CH_3$ | $CH_3$ | |
| 9.2 | H | Cl | $CH_3$ | $C_2H_5$ | |
| 9.3 | H | Cl | $CH_3$ | $CH_2OH$ | |
| 9.4 | H | Cl | $CH_3$ | $CH_2Cl$ | |
| 9.5 | H | Cl | $CH_3$ | $CH_2OCOCH_3$ | |
| 9.6 | H | Cl | $CH_3$ | $CH_3$ | |
| 9.7 | H | Cl | $CH_3$ | $CH_3$ | |
| 9.8 | H | Cl | $CH_3$ | $CH_3$ | |
| 9.9 | H | Cl | $CH_3$ | $CH_3$ | |
| 9.10 | H | Cl | $CH_3$ | $CH_2OH$ | |
| 9.11 | H | Cl | $CH_3$ | $CH_2Cl$ | |
| 9.12 | H | Cl | $CH_3$ | $CH_2Br$ | |
| 9.13 | H | Cl | $CH_3$ | $CH_2OCH_3$ | |
| 9.14 | H | Cl | $CH_3$ | $CH_2OC_2H_5$ | |
| 9.15 | H | Cl | $CH_3$ | $CH_2CN$ | |
| 9.16 | H | Cl | $CH_3$ | $CH_2OCOCH_3$ | |
| 9.17 | H | Cl | $CH_3$ | $CH_2OCOCH_2Cl$ | |
| 9.18 | H | Cl | $CH_3$ | $CH_2OCOC_2H_5$ | |
| 9.19 | H | Cl | $CH_3$ | $COOH$ | |
| 9.20 | H | Cl | $CH_3$ | $COOCH_3$ | |
| 9.21 | H | Cl | $CH_3$ | $COOCH_3$ | |
| 9.22 | H | Cl | $CH_3$ | $COOCH(CH_3)_2$ | |
| 9.23 | H | Cl | $CH_3$ | $COOCH_2CH=CH_2$ | |
| 9.24 | H | Cl | $CH_3$ | $COOCH_2C\equiv CH$ | |
| 9.25 | H | Cl | $CH_3$ | $COONH_2$ | |
| 9.26 | H | Cl | $CH_3$ | $COONHCH_3$ | |
| 9.27 | Cl | Cl | $CH_3$ | $CH_3$ | |
| 9.28 | Cl | Cl | $CH_3$ | $C_2H_5$ | |
| 9.29 | Cl | Cl | $CH_3$ | $CH_2OH$ | |
| 9.30 | Cl | Cl | $CH_3$ | $CH_3$ | |
| 9.31 | Cl | Cl | $CH_3$ | $CH_2Cl$ | |
| 9.32 | Cl | Cl | $CH_3$ | $CH_2Br$ | |
| 9.33 | Cl | Cl | $CH_3$ | $CH_2OCH_3$ | |
| 9.34 | Cl | Cl | $CH_3$ | $CH_2CN$ | |
| 9.35 | Cl | Cl | $CH_3$ | $CH_2OCOCH_3$ | |
| 9.36 | Cl | Cl | $CH_3$ | $CH_2OCOCH_2Cl$ | |
| 9.37 | Cl | Cl | $CH_3$ | $COOH$ | |
| 9.38 | Cl | Cl | $CH_3$ | $COOCH_3$ | |
| 9.39 | Cl | Cl | $CH_3$ | $COOC_2H_5$ | |
| 9.40 | Cl | Cl | $CH_3$ | $COOCH_3$ | |
| 9.41 | Cl | Cl | $CH_3$ | $COOCH_3$ | |
| 9.42 | Cl | Cl | $CH_3$ | $COOCH(CH_3)_2$ | |
| 9.43 | Cl | Cl | $CH_3$ | $COOCH_2CH=CH_2$ | |
| 9.44 | Cl | Cl | $CH_3$ | $COOCH_2C\equiv CH$ | |
| 9.45 | Cl | Cl | $CH_3$ | $CONH_2$ | |
| 9.46 | Cl | Cl | $CH_3$ | $CON(CH_3)_2$ | |
| 9.47 | Cl | Cl | $CH_3$ | $CN$ | |
| 9.48 | Cl | Cl | $CH_3$ | $CHO$ | |
| 9.49 | Cl | Cl | $CH_3$ | $CH=NOH$ | |
| 9.50 | Cl | Cl | $CH_3$ | $CH=NOCH_3$ | |
| 9.51 | Cl | Cl | $CH_3$ | $CH_3$ | |
| 9.52 | Cl | Cl | $CH_3$ | $COOCH_3$ | |
| 9.53 | F | Cl | $CH_3$ | $CH_3$ | |
| 9.54 | F | Cl | $CH_3$ | $C_2H_5$ | |
| 9.55 | F | Cl | $CH_3$ | $CH_2OH$ | |
| 9.56 | F | Cl | $CH_3$ | $CH_3$ | |
| 9.57 | F | Cl | $CH_3$ | $CH_2Cl$ | |
| 9.58 | F | Cl | $CH_3$ | $CH_2Br$ | |
| 9.59 | F | Cl | $CH_3$ | $CH_2OCH_3$ | |
| 9.60 | F | Cl | $CH_3$ | $CH_2CN$ | |
| 9.61 | F | Cl | $CH_3$ | $CH_2OCOCH_3$ | |
| 9.62 | F | Cl | $CH_3$ | $CH_2OCOCH_2Cl$ | |
| 9.63 | F | Cl | $CH_3$ | $COOH$ | |
| 9.64 | F | Cl | $CH_3$ | $COOCH_3$ | |
| 9.65 | F | Cl | $CH_3$ | $COOC_2H_5$ | |
| 9.66 | F | Cl | $CH_3$ | $COOCH_3$ | |
| 9.67 | F | Cl | $CH_3$ | $COOCH_3$ | |
| 9.68 | F | Cl | $CH_3$ | $COOC_2H_5$ | |
| 9.69 | F | Cl | $CH_3$ | $COOC_3H_7(n)$ | |
| 9.70 | F | Cl | $CH_3$ | $COOCH(CH_3)_2$ | |
| 9.71 | F | Cl | $CH_3$ | $COOC_4H_9(n)$ | |
| 9.72 | F | Cl | $CH_3$ | $COOCH_2CH(CH_3)_2$ | |
| 9.73 | F | Cl | $CH_3$ | $COOCH(CH_3)C_2H_5$ | |
| 9.74 | F | Cl | $CH_3$ | $COOC_5H_{11}(n)$ | |
| 9.75 | F | Cl | $CH_3$ | $COOCH_2CH=CH_2$ | |
| 9.76 | F | Cl | $CH_3$ | $COOCH_2C\equiv CH$ | |
| 9.77 | F | Cl | $CH_3$ | $COO$-cyclohexyl | |
| 9.78 | F | Cl | $CH_3$ | $COOCH_2$-phenyl | |
| 9.79 | F | Cl | $CH_3$ | $COOCH_3$ | |
| 9.80 | F | Cl | $CH_3$ | $COOCH(CH_3)_2$ | |
| 9.81 | F | Cl | $CH_3$ | $CONHSO_2CH_3$ | |
| 9.82 | F | Cl | $CH_3$ | $CH=NOCH_3$ | |
| 9.83 | F | Cl | $CH_3$ | $CSNH_2$ | |
| 9.84 | F | Cl | $CH_3$ | $CHO$ | |
| 9.85 | F | Cl | $CH_3$ | $CN$ | |
| 9.86 | F | F | $CH_3$ | $CH_2OH$ | |
| 9.87 | F | F | $CH_3$ | $CH_2Cl$ | |
| 9.88 | F | F | $CH_3$ | $COOH$ | |
| 9.89 | F | F | $CH_3$ | $COOCH_3$ | |
| 9.90 | F | F | $CH_3$ | $COOCH(CH_3)_2$ | |
| 9.91 | F | CN | $CH_3$ | $CH_3$ | |
| 9.92 | F | CN | $CH_3$ | $CH_2OH$ | |
| 9.93 | F | CN | $CH_3$ | $COOH$ | |
| 9.94 | F | CN | $CH_3$ | $COOCH_3$ | |
| 9.95 | F | CN | $CH_3$ | $COOCH(CH_3)_2$ | |
| 9.96 | F | Br | $CH_3$ | $CH_3$ | |
| 9.97 | F | Br | $CH_3$ | $CH_3$ | |
| 9.98 | F | Br | $CH_3$ | $COOCH_3$ | |
| 9.99 | F | Cl | $CH_3$ | $CH_2OH$ | |
| 9.100 | F | Cl | $CH_3$ | $COOCH_3$ | |

TABLE 10

Compounds of the formula It

| Comp. No. | R | $R_1$ | $R_3$ | Physical data |
|---|---|---|---|---|
| 10.1 | H | Cl | $CH_3$ | |
| 10.2 | H | Cl | $CH_2OH$ | |
| 10.3 | H | Cl | $CH_2Cl$ | |
| 10.4 | H | Cl | $CH_2Br$ | |
| 10.5 | H | Cl | $CH_2OCH_3$ | |
| 10.6 | H | Cl | $CH_2CN$ | |
| 10.7 | H | Cl | $CH_2OC_2H_5$ | |
| 10.8 | H | Cl | COOH | |
| 10.9 | H | Cl | $COOCH_3$ | |
| 10.10 | H | Cl | $COOC_2H_5$ | |
| 10.11 | H | Cl | $COOCH(CH_3)_2$ | |
| 10.12 | H | Cl | $COOCH_2CH=CH_2$ | |
| 10.13 | H | Cl | $COOCH_2C\equiv CH$ | |
| 10.14 | H | Cl | $CONH_2$ | |
| 10.15 | H | Cl | $CONHCH_3$ | |
| 10.16 | H | Cl | $CSNH_2$ | |
| 10.17 | Cl | Cl | $CH_3$ | |
| 10.18 | Cl | Cl | $CH_2OH$ | |
| 10.19 | Cl | Cl | $CH_2Cl$ | |
| 10.20 | Cl | Cl | $CH_3$ | |
| 10.21 | Cl | Cl | $CH_2OH$ | |
| 10.22 | Cl | Cl | $CH_2Cl$ | |
| 10.23 | Cl | Cl | $CH_2Br$ | |
| 10.24 | Cl | Cl | $CH_2OCH_3$ | |
| 10.25 | Cl | Cl | COOH | |
| 10.26 | Cl | Cl | $COOCH_3$ | |
| 10.27 | Cl | Cl | $COOCH(CH_3)_2$ | |
| 10.28 | Cl | Cl | $COOCH_2CH=CH_2$ | |
| 10.29 | Cl | Cl | $CONH_2$ | |
| 10.30 | F | Cl | $CH_3$ | |
| 10.31 | F | Cl | $CH_2OH$ | |
| 10.32 | F | Cl | $CH_2Cl$ | |
| 10.33 | F | Cl | $CH_2Br$ | |
| 10.34 | F | Cl | $C_2H_5$ | |
| 10.35 | F | Cl | $CH_2OCH_3$ | |
| 10.36 | F | Cl | $CH_2OCOCH_3$ | |
| 10.37 | F | Cl | $CH_2OCOCH_2Cl$ | |
| 10.38 | F | Cl | COOH | |
| 10.39 | F | Cl | $COOCH_3$ | |
| 10.40 | F | Cl | $COOC_2H_5$ | |
| 10.41 | F | Cl | $COOC_3H_7(n)$ | |
| 10.42 | F | Cl | $COOCH(CH_3)_2$ | |
| 10.43 | F | Cl | $COOC_4H_9(n)$ | |
| 10.44 | F | Cl | $COOCH_2CH(CH_3)_2$ | |
| 10.45 | F | Cl | $COOCH(CH_3)C_2H_5$ | |
| 10.46 | F | Cl | $COOCH_2CH_2CH_2COOCH_3$ | |
| 10.47 | F | Cl | $COOCH_2CH=CH_2$ | |
| 10.48 | F | Cl | $COOCH_2C\equiv CH$ | |
| 10.49 | F | Cl | COO-cyclohexyl | |
| 10.50 | F | Cl | $COOCH_2$-phenyl | |
| 10.51 | F | Cl | CN | |
| 10.52 | F | Cl | $CSNH_2$ | |
| 10.53 | F | Cl | $CONH_2$ | |
| 10.54 | F | Cl | $CONHCH_3$ | |
| 10.55 | F | Cl | $CON(CH_3)_2$ | |
| 10.56 | F | Cl | CH=NOH | |
| 10.57 | F | Cl | $CH=NOCH_3$ | |
| 10.58 | F | F | $CH_3$ | |
| 10.59 | F | F | $CH_2Cl$ | |
| 10.60 | F | F | $CH_2OH$ | |
| 10.61 | F | F | COOH | |
| 10.62 | F | F | $COOCH_3$ | |
| 10.63 | F | F | $COOCH(CH_3)_2$ | |
| 10.64 | F | F | $CH_2COCH_3$ | |
| 10.65 | F | Br | $CH_3$ | |
| 10.66 | F | Br | $COOCH_3$ | |
| 10.67 | F | Br | $COOCH(CH_3)_2$ | |
| 10.68 | F | CN | $CH_3$ | |
| 10.69 | F | CN | $COOCH_3$ | |
| 10.70 | F | CN | $COOCH(CH_3)_2$ | |
| 10.71 | F | CN | CHO | |
| 10.72 | F | CN | $CONH_2$ | |
| 10.73 | F | CN | $CONHCH_3$ | |

TABLE 11

Compounds of the formula Iu

| Comp. No. | R | $R_1$ | $R_3$ | Physical data |
|---|---|---|---|---|
| 11.1 | H | Cl | $CH_3$ | |
| 11.2 | H | Cl | $CH_2OH$ | |
| 11.3 | H | Cl | $CH_2Cl$ | |
| 11.4 | H | Cl | $CH_2Br$ | |
| 11.5 | H | Cl | $CH_2OCH_3$ | |
| 11.6 | H | Cl | $CH_2CN$ | |
| 11.7 | H | Cl | $CH_2OC_2H_5$ | |
| 11.8 | H | Cl | COOH | |
| 11.9 | H | Cl | $COOCH_3$ | |
| 11.10 | H | Cl | $COOC_2H_5$ | |
| 11.11 | H | Cl | $COOCH(CH_3)_2$ | |
| 11.12 | H | Cl | $COOCH_2CH=CH_2$ | |
| 11.13 | H | Cl | $COOCH_2C\equiv CH$ | |
| 11.14 | H | Cl | $CONH_2$ | |
| 11.15 | H | Cl | $CONHCH_3$ | |
| 11.16 | H | Cl | $CSNH_2$ | |

TABLE 11-continued

Compounds of the formula Iu $$\text{(Iu)}$$

| Comp. No. | R | $R_1$ | $R_3$ | Physical data |
|---|---|---|---|---|
| 11.17 | Cl | Cl | $CH_3$ | |
| 11.18 | Cl | Cl | $CH_2OH$ | |
| 11.19 | Cl | Cl | $CH_2Cl$ | |
| 11.20 | Cl | Cl | $CH_3$ | |
| 11.21 | Cl | Cl | $CH_2OH$ | |
| 11.22 | Cl | Cl | $CH_2Cl$ | |
| 11.23 | Cl | Cl | $CH_2Br$ | |
| 11.24 | Cl | Cl | $CH_2OCH_3$ | |
| 11.25 | Cl | Cl | COOH | |
| 11.26 | Cl | Cl | $COOCH_3$ | |
| 11.27 | Cl | Cl | $COOCH(CH_3)_2$ | |
| 11.28 | Cl | Cl | $COOCH_2CH=CH_2$ | |
| 11.29 | Cl | Cl | $CONH_2$ | |
| 11.30 | F | Cl | $CH_3$ | |
| 11.31 | F | Cl | $CH_2OH$ | |
| 11.32 | F | Cl | $CH_2Cl$ | |
| 11.33 | F | Cl | $CH_2Br$ | |
| 11.34 | F | Cl | $C_2H_5$ | |
| 11.35 | F | Cl | $CH_2OCH_3$ | |
| 11.36 | F | Cl | $CH_2OCOCH_3$ | |
| 11.37 | F | Cl | $CH_2OCOCH_2Cl$ | |
| 11.38 | F | Cl | COOH | |
| 11.39 | F | Cl | $COOCH_3$ | |
| 11.40 | F | Cl | $COOC_2H_5$ | |
| 11.41 | F | Cl | $COOC_3H_7(n)$ | |
| 11.42 | F | Cl | $COOCH(CH_3)_2$ | |
| 11.43 | F | Cl | $COOC_4H_9(n)$ | |
| 11.44 | F | Cl | $COOCH_2CH(CH_3)_2$ | |
| 11.45 | F | Cl | $COOCH(CH_3)C_2H_5$ | |
| 11.46 | F | Cl | $COOCH_2CH_2CH_2COOCH_3$ | |
| 11.47 | F | Cl | $COOCH_2CH=CH_2$ | |
| 11.48 | F | Cl | $COOCH_2C\equiv CH$ | |
| 11.49 | F | Cl | COO—cyclohexyl | |
| 11.50 | F | Cl | $COOCH_2$—phenyl | |
| 11.51 | F | Cl | CN | |
| 11.52 | F | Cl | $CSNH_2$ | |
| 11.53 | F | Cl | $CONH_2$ | |
| 11.54 | F | Cl | $CONHCH_3$ | |
| 11.55 | F | Cl | $CON(CH_3)_2$ | |
| 11.56 | F | Cl | CH=NOH | |
| 11.57 | F | Cl | $CH=NOCH_3$ | |
| 11.58 | F | F | $CH_3$ | |
| 11.59 | F | F | $CH_2Cl$ | |
| 11.60 | F | F | $CH_2OH$ | |
| 11.61 | F | F | COOH | |
| 11.62 | F | F | $COOCH_3$ | |
| 11.63 | F | F | $COOCH(CH_3)_2$ | |
| 11.64 | F | F | $CH_2COCH_3$ | |
| 11.65 | F | Br | $CH_3$ | |
| 11.66 | F | Br | $COOCH_3$ | |
| 11.67 | F | Br | $COOCH(CH_3)_2$ | |
| 11.68 | F | CN | $CH_3$ | |
| 11.69 | F | CN | $COOCH_3$ | |
| 11.70 | F | CN | $COOCH(CH_3)_2$ | |
| 11.71 | F | CN | CHO | |
| 11.72 | F | CN | $CONH_2$ | |
| 11.73 | F | CN | $CONHCH_3$ | |

TABLE 12

Compounds of the formula Iv $$\text{(Iv)}$$

| Comp. No. | R | $R_1$ | $R_2$ | $R_3$ | Physical data |
|---|---|---|---|---|---|
| 12.1 | H | Cl | $CH_3$ | $CH_3$ | |
| 12.2 | H | Cl | $CH_3$ | $C_2H_5$ | |
| 12.3 | H | Cl | $CH_3$ | $CH_2OH$ | |
| 12.4 | H | Cl | $CH_3$ | $CH_2Cl$ | |
| 12.5 | H | Cl | $CH_3$ | $CH_2OCOCH_3$ | |
| 12.6 | H | Cl | $CH_3$ | $CH_3$ | |
| 12.7 | H | Cl | $CH_3$ | $CH_3$ | |
| 12.8 | H | Cl | $CH_3$ | $CH_3$ | |
| 12.9 | H | Cl | $CH_3$ | $CH_3$ | |
| 12.10 | H | Cl | $CH_3$ | $CH_2OH$ | |
| 12.11 | H | Cl | $CH_3$ | $CH_2Cl$ | |
| 12.12 | H | Cl | $CH_3$ | $CH_2Br$ | |
| 12.13 | H | Cl | $CH_3$ | $CH_2OCH_3$ | |
| 12.14 | H | Cl | $CH_3$ | $CH_2OC_2H_5$ | |
| 12.15 | H | Cl | $CH_3$ | $CH_2CN$ | |
| 12.16 | H | Cl | $CH_3$ | $CH_2OCOCH_3$ | |
| 12.17 | H | Cl | $CH_3$ | $CH_2OCOCH_2Cl$ | |
| 12.18 | H | Cl | $CH_3$ | $CH_2OCOC_2H_5$ | |
| 12.19 | H | Cl | $CH_3$ | COOH | |
| 12.20 | H | Cl | $CH_3$ | $COOCH_3$ | |
| 12.21 | H | Cl | $CH_3$ | $COOCH_3$ | |
| 12.22 | H | Cl | $CH_3$ | $COOCH(CH_3)_2$ | |
| 12.23 | H | Cl | $CH_3$ | $COOCH_2CH=CH_2$ | |
| 12.24 | H | Cl | $CH_3$ | $COOCH_2C\equiv CH$ | |
| 12.25 | H | Cl | $CH_3$ | $COONH_2$ | |
| 12.26 | H | Cl | $CH_3$ | $COONHCH_3$ | |
| 12.27 | Cl | Cl | $CH_3$ | $CH_3$ | |
| 12.28 | Cl | Cl | $CH_3$ | $C_2H_5$ | |
| 12.29 | Cl | Cl | $CH_3$ | $CH_2OH$ | |
| 12.30 | Cl | Cl | $CH_3$ | $CH_3$ | |
| 12.31 | Cl | Cl | $CH_3$ | $CH_2Cl$ | |
| 12.32 | Cl | Cl | $CH_3$ | $CH_2Br$ | |
| 12.33 | Cl | Cl | $CH_3$ | $CH_2OCH_3$ | |

TABLE 12-continued

Compounds of the formula Iv

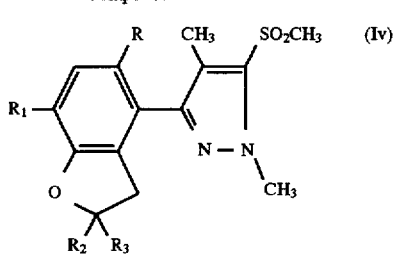

| Comp. No. | R | $R_1$ | $R_2$ | $R_3$ | Physical data |
|---|---|---|---|---|---|
| 12.34 | Cl | Cl | $CH_3$ | $CH_2CN$ | |
| 12.35 | Cl | Cl | $CH_3$ | $CH_2OCOCH_3$ | |
| 12.36 | Cl | Cl | $CH_3$ | $CH_2OCOCH_2Cl$ | |
| 12.37 | Cl | Cl | $CH_3$ | COOH | |
| 12.38 | Cl | Cl | $CH_3$ | $COOCH_3$ | |
| 12.39 | Cl | Cl | $CH_3$ | $COOC_2H_5$ | |
| 12.40 | Cl | Cl | $CH_3$ | $COOCH_3$ | |
| 12.41 | Cl | Cl | $CH_3$ | $COOCH_3$ | |
| 12.42 | Cl | Cl | $CH_3$ | $COOCH(CH_3)_2$ | |
| 12.43 | Cl | Cl | $CH_3$ | $COOCH_2CH=CH_2$ | |
| 12.44 | Cl | Cl | $CH_3$ | $COOCH_2C\equiv CH$ | |
| 12.45 | Cl | Cl | $CH_3$ | $CONH_2$ | |
| 12.46 | Cl | Cl | $CH_3$ | $CON(CH_3)_2$ | |
| 12.47 | Cl | Cl | $CH_3$ | CN | |
| 12.48 | Cl | Cl | $CH_3$ | CHO | |
| 12.49 | Cl | Cl | $CH_3$ | CH=NOH | |
| 12.50 | Cl | Cl | $CH_3$ | $CH=NOCH_3$ | |
| 12.51 | Cl | Cl | $CH_3$ | $CH_3$ | |
| 12.52 | Cl | Cl | $CH_3$ | $COOCH_3$ | |
| 12.53 | F | Cl | $CH_3$ | $CH_3$ | |
| 12.54 | F | Cl | $CH_3$ | $C_2H_5$ | |
| 12.55 | F | Cl | $CH_3$ | $CH_2OH$ | |
| 12.56 | F | Cl | $CH_3$ | $CH_3$ | |
| 12.57 | F | Cl | $CH_3$ | $CH_2Cl$ | |
| 12.58 | F | Cl | $CH_3$ | $CH_2Br$ | |
| 12.59 | F | Cl | $CH_3$ | $CH_2OCH_3$ | |
| 12.60 | F | Cl | $CH_3$ | $CH_2CN$ | |
| 12.61 | F | Cl | $CH_3$ | $CH_2OCOCH_3$ | |
| 12.62 | F | Cl | $CH_3$ | $CH_2OCOCH_2Cl$ | |
| 12.63 | F | Cl | $CH_3$ | COOH | |
| 12.64 | F | Cl | $CH_3$ | $COOCH_3$ | |
| 12.65 | F | Cl | $CH_3$ | $COOC_2H_5$ | |
| 12.66 | F | Cl | $CH_3$ | $COOCH_3$ | |
| 12.67 | F | Cl | $CH_3$ | $COOCH_3$ | |
| 12.68 | F | Cl | $CH_3$ | $COOC_2H_5$ | |
| 12.69 | F | Cl | $CH_3$ | $COOC_3H_7(n)$ | |
| 12.70 | F | Cl | $CH_3$ | $COOCH(CH_3)_2$ | |
| 12.71 | F | Cl | $CH_3$ | $COOC_4H_9(n)$ | |
| 12.72 | F | Cl | $CH_3$ | $COOCH_2CH(CH_3)_2$ | |
| 12.73 | F | Cl | $CH_3$ | $COOCH(CH_3)C_2H_5$ | |
| 12.74 | F | Cl | $CH_3$ | $COOC_5H_{11}(n)$ | |
| 12.75 | F | Cl | $CH_3$ | $COOCH_2CH=CH_2$ | |
| 12.76 | F | Cl | $CH_3$ | $COOCH_2C\equiv CH$ | |
| 12.77 | F | Cl | $CH_3$ | 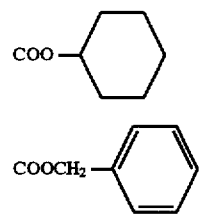 | |
| 12.78 | F | Cl | $CH_3$ | $COOCH_2$-phenyl | |
| 12.79 | F | Cl | $CH_3$ | $COOCH_3$ | |
| 12.80 | F | Cl | $CH_3$ | $COOCH(CH_3)_2$ | |
| 12.81 | F | Cl | $CH_3$ | $CONHSO_2CH_3$ | |
| 12.82 | F | Cl | $CH_3$ | $CH=NOCH_3$ | |
| 12.83 | F | Cl | $CH_3$ | $CSNH_2$ | |

TABLE 12-continued

Compounds of the formula Iv

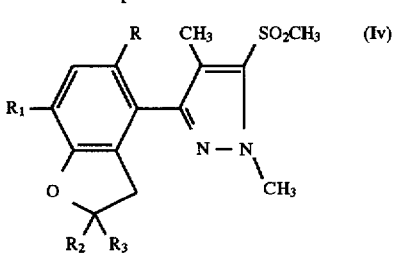

| Comp. No. | R | $R_1$ | $R_2$ | $R_3$ | Physical data |
|---|---|---|---|---|---|
| 12.84 | F | Cl | $CH_3$ | CHO | |
| 12.85 | F | Cl | $CH_3$ | CN | |
| 12.86 | F | F | $CH_3$ | $CH_2OH$ | |
| 12.87 | F | F | $CH_3$ | $CH_2Cl$ | |
| 12.88 | F | F | $CH_3$ | COOH | |
| 12.89 | F | F | $CH_3$ | $COOCH_3$ | |
| 12.90 | F | F | $CH_3$ | $COOCH(CH_3)_2$ | |
| 12.91 | F | CN | $CH_3$ | $CH_3$ | |
| 12.92 | F | CN | $CH_3$ | $CH_2OH$ | |
| 12.93 | F | CN | $CH_3$ | COOH | |
| 12.94 | F | CN | $CH_3$ | $COOCH_3$ | |
| 12.95 | F | CN | $CH_3$ | $COOCH(CH_3)_2$ | |
| 12.96 | F | Br | $CH_3$ | $CH_3$ | |
| 12.97 | F | Br | $CH_3$ | $CH_3$ | |
| 12.98 | F | Br | $CH_3$ | $COOCH_3$ | |
| 12.99 | F | Cl | $CH_3$ | $CH_2OH$ | |
| 12.100 | F | Cl | $CH_3$ | $COOCH_3$ | |

Formulation Examples of active ingredients of the formula I (%=percent by weight)

| F1. Emulsion concentrates | a) | b) | c) | d) |
|---|---|---|---|---|
| Active ingredient in acc. with Tables 1–12 | 5% | 10% | 25% | 50% |
| Calcium dodecylbenzenesulfonate | 6% | 8% | 6% | 8% |
| Castor oil polyglycol ether (36 mol of EO) | 4% | — | 4% | 4% |
| Octylphenyl polyglycol ether (7–8 mol of EO) | — | 4% | — | 2% |
| Cyclohexanone | — | — | 10% | 20% |
| Arom. hydrocarbon mixture $C_9-C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| Active ingredient in acc. with Tables 1–12 | 5% | 10% | 50% | 90% |
| 1-Methoxy-3-(3-methoxy-propoxy)propane | — | 20% | 20% | — |
| Polyethylene glycol MW 400 | 20% | 10% | — | — |
| N-Methyl-2-pyrrolidone | — | — | 30% | 10% |
| Aromatic hydrocarbon mixture $C_9-C_{12}$ | 75% | 60% | — | — |

The solutions are suitable for use in the form of microdrops.

| F3. Wettable powders | a) | b) | c) | d) |
|---|---|---|---|---|
| Active ingredient in acc. with Tables 1–12 | 5% | 25% | 50% | 80% |

-continued

| F3. Wettable powders | a) | b) | c) | d) |
|---|---|---|---|---|
| Sodium ligninsulfonate | 4% | — | 3% | — |
| Sodium lauryl sulfate | 2% | 3% | — | 4% |
| Sodium diisobutylnaphthalene sulfonate | — | 6% | 5% | 6% |
| Octylphenyl polyglycol ether (7–8 mol of EO) | — | 1% | 2% | — |
| Highly-disperse silica | 1% | 3% | 5% | 10% |
| Kaolin | 88% | 62% | 35% | — |

The active ingredient is mixed thoroughly with the additives and the mixture is ground thoroughly in a suitable mill. This gives wettable powders which can be diluted with water to give suspensions of any desired concentration.

| F4. Coated granules | a) | b) | c) |
|---|---|---|---|
| Active ingredient in acc. with Tables 1–12 | 0.1% | 5% | 15% |
| Highly-disperse silica | 0.9% | 2% | 2% |
| Inorganic carrier (∅ 0.1–1 mm) for example $CaCO_3$ or $SiO_2$ | 99.0% | 93% | 83% |

The active ingredient is dissolved in methylene chloride, the solution is sprayed onto the carrier, and the solvent is subsequently evaporated in vacuo.

| F5. Coated granules | a) | b) | c) |
|---|---|---|---|
| Active ingredient in acc. with Tables 1–12 | 0.1% | 5% | 15% |
| Polyethylene glycol MW 200 | 1.0% | 2% | 3% |
| Highly-disperse silica | 0.9% | 1% | 2% |
| Inorganic carrier (∅ 0.1–1 mm) for example $CaCO_3$ or $SiO_2$ | 98.0% | 92% | 80% |

In a mixer, the finely ground active ingredient is applied uniformly to the carrier which has been moistened with polyethylene glycol. This gives dust-free coated granules.

| F6. Extruder granules | a) | b) | c) | d) |
|---|---|---|---|---|
| Active ingredient in acc. with Tables 1–12 | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The active ingredient is mixed with the additives, and the mixture is ground and moistened with water. This mixture is extruded and subsequently dried in a stream of air.

| F7. Dusts | a) | b) | c) |
|---|---|---|---|
| Active ingredient in acc. with Tables 1–12 | 0.1% | 1% | 5% |
| Talc | 39.9% | 49% | 35% |
| Kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| Active ingredient in acc. with Tables 1–12 | 3% | 10% | 25% | 50% |
| Ethylene glycol | 5% | 5% | 5% | 5% |
| Nonylphenyl polyglycol ether (15 mol of EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely-ground active ingredient is mixed intimately with the additives. This gives a suspension concentrate from which suspensions of any desired concentration can be prepared by dilution with water.

BIOLOGICAL EXAMPLES

Example B1

Herbicidal action before emergence of the plants (pre-emergence action)

Monocotyledonous and dicotyledonous test plants are sown in standard soil in plastic pots. Immediately after sowing, the test substances are sprayed on (500 l of water/ha) in the form of an aqueous suspension or emulsion prepared from a 25% emulsion concentrate (Example F1, c)), to reflect a dosage of 500 g of a.s./ha (Nos. 1.59, 1.68, 1.74 and 1.76) or 2000 g a.s./ha (Nos. 1.77, 1.78 and 1.80). The test plants are subsequently grown in the greenhouse under optimal conditions. After a test period of 3 weeks, the experiment is evaluated using a nine-step scale (1=complete destruction, 9=no action). Scores of 1 to 4 (in particular 1 to 3) denote a good to very good herbicidal activity.

Test plants: Setaria, Sinapis, Solanum, Stellaria, Ipomoea.

The compounds according to the invention have a good herbicidal activity.

Examples for the good herbicidal activity of the compounds of the formula I are shown in Table B1.

TABLE B1

| Active ingredient No. | Pre-emergence activity: Test plant: | | | | |
|---|---|---|---|---|---|
| | Setaria | Sinapis | Solanum | Stellaria | Ipomoea |
| 1.59 | 1 | 2 | 1 | 1 | 4 |
| 1.68 | 3 | 7 | 1 | 2 | 4 |
| 1.74 | 4 | 2 | 1 | 2 | 4 |
| 1.76 | 4 | 7 | 1 | 4 | 7 |
| 1.77 | 1 | 3 | — | 1 | — |
| 1.78 | 1 | 3 | — | 1 | — |
| 1.80 | 1 | 1 | — | 1 | — |

The same results are obtained if the compounds of the formula I are formulated in accordance with Examples F2 to F8.

Example B2

Post-emergence herbicidal action

Monocotyledonous and dicotyledonous test plants are grown in the greenhouse in plastic pots containing standard soil and, in the 4- to 6-leaf stage, sprayed with an aqueous suspension or emulsion of the test substances of the formula I, prepared from a 25% emulsion concentrate (Example F1, c)) to reflect a dosage of 500 g of a.s./ha (Nos. 1.59, 1.68, 1.74 and 1.76) or 2000 g a.s./ha (No. 1.77, 1.78 and 1.80) (500 l of water/ha). The test plants are subsequently grown on in the greenhouse under optimal conditions. After a test period of approximately 18 days, the experiment is evaluated using a nine-step scale (1=complete destruction, 9=no action). Scores of 1 to 4 (in particular 1 to 3) denote a good to very good herbicidal activity.

Test plants: Setaria, Sinapis, Solanum, Stellaria, Ipomoea.

In this test, again, the compounds of the formula I have a potent herbicidal activity.

Examples of the good herbicidal activity of the compounds of the formula I are shown in Table B2.

TABLE B2

| Active | Post-emergence activity: Test plant: | | | | |
|---|---|---|---|---|---|
| ingredient No. | Setaria | Sinapis | Solanum | Stellaria | Ipomoea |
| 1.59 | 1 | 1 | 1 | 1 | 1 |
| 1.68 | 4 | 1 | 1 | 2 | 1 |
| 1.74 | 4 | 1 | 1 | 3 | 1 |
| 1.76 | 2 | 1 | 1 | 3 | 1 |
| 1.77 | 1 | 1 | — | 1 | — |
| 1.78 | 1 | 1 | — | 1 | — |
| 1.80 | 1 | 1 | — | 1 | — |

The same results are obtained when the compounds of the formula I are formulated in accordance with Examples F2 to F8.

What is claimed is:

1. A compound of the formula I

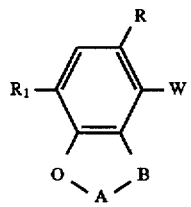

(I)

in which

R is hydrogen, fluorine or chlorine;

$R_1$ is hydrogen, halogen, trifluoromethyl, $C_1$–$C_4$haloalkoxy, cyano, nitro or amino;

A-B is a group

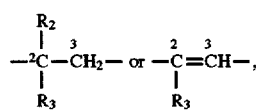

in which the 2 carbon atom is bonded to the oxygen atom;

W is a group

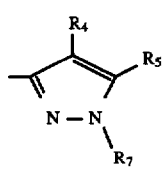

(W1)

or

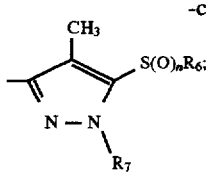

(W2)

$R_2$ is hydrogen or $C_1$–$C_4$alkyl;

$R_3$ is $C_1$–$C_6$alkyl, $C_1$–$C_6$haloalkyl, cyano-$C_1$–$C_4$alkyl, hydroxy-$C_1$–$C_6$alkyl, $C_1$–$C_6$alkoxy-$C_1$–$C_6$alkyl, $C_3$–$C_6$alkenyloxy-$C_1$–$C_4$alkyl, $C_3$–$C_6$alkynyloxy-$C_1$–$C_4$alkyl, $C_1$–$C_6$alkylcarbonyloxy-$C_1$–$C_6$alkyl, carboxyl, $C_1$–$C_6$alkoxycarbonyl, $C_1$–$C_6$haloalkoxycarbonyl, $C_3$–$C_6$alkenyloxycarbonyl, $C_3$–$C_6$alkynyloxycarbonyl, $C_3$–$C_6$cycloalkoxycarbonyl, $C_1$–$C_4$alkoxy-$C_1$–$C_4$alkoxycarbonyl, $C_1$–$C_4$alkylaminocarbonyl, di-$C_1$–$C_4$alkylaminocarbonyl, aminocarbonyl, benzyloxycarbonyl, phenyloxycarbonyl, $C_1$–$C_4$alkyl-$SO_2NHC(O)$—, $C_1$–$C_6$alkyl-$ON=CH$—, $C_1$–$C_6$alkoxycarbonyl-$C_1$–$C_4$alkyl, $C_1C_3$alkylcarbonyl, $ClC(O)$—, $NH_2C(S)$—, $OHC$— or cyano;

$R_4$ is hydrogen, fluorine, chlorine or bromine;

$R_5$ is carboxyl, $C_1$–$C_6$alkoxycarbonyl, $NH_2C(O)$—, $NH_2C(S)$—, $HON=CH$—, $OHC$— or cyano;

$R_6$ is hydrogen or $C_1$–$C_4$alkyl;

n is 0, 1 or 2, with the proviso that n is 0 if $R_6$ is hydrogen; and $R_7$ is hydrogen or $C_1$–$C_4$alkyl, and agronomically acceptable salts and stereoisomers thereof.

2. A compound according to claim 1 in which $R_1$ is hydrogen, fluorine, chlorine, bromine, trifluoromethyl or cyano.

3. A compound according to claim 1 in which R is hydrogen or fluorine.

4. A compound according to claim 3 in which R is fluorine.

5. A compound according to claim 1 where W is a group

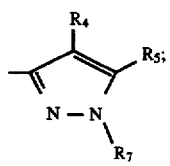

(W1)

$R_4$, $R_5$ and $R_7$ are as defined in claim 1.

6. A compound according to claim 5 in which $R_7$ is hydrogen, methyl or ethyl.

7. A compound according to claim 5 in which $R_5$ is carboxyl, $C_1$–$C_3$alkoxycarbonyl, $NH_2C(S)$—, $HON=CH$—, $OHC$— or cyano.

8. A compound according to claim 7 in which $R_5$ is cyano.

9. A compound according to claim 5 in which $R_4$ is hydrogen or chlorine.

10. A compound according to claim 1 in which W is a group (W2)

$$\begin{array}{c} CH_3 \\ | \\ \diagup\!\!\!\diagdown\!\!-S(O)_nR_6; \\ | \quad | \\ N-N \\ | \\ R_7 \end{array}$$

and $R_6$, $R_7$ and n are as defined in claim 1.

11. A compound according to claim 10 in which n is 0 or 2.

12. A compound according to claim 10 in which $R_6$ is methyl.

13. A compound according to claim 10 in which $R_7$ is methyl or ethyl.

14. A compound according to claim 13 in which $R_7$ is methyl.

15. A compound according to claim 1 in which A-B is a group $$\begin{array}{c} R_2 \\ 2| \quad 3 \\ -C-CH_2-; \\ | \\ R_3 \end{array}$$

$R_2$ is hydrogen or methyl; and $R_3$ is hydrogen, $C_1$–$C_3$alkyl, $C_1$— or $C_2$haloalkyl, cyano-$C_1$–$C_4$alkyl, $C_1$–$C_3$alkylcarbonyloxy-$C_1$— or —$C_2$alkyl, carboxyl, $C_1$–$C_3$alkoxycarbonyl, $C_1$-$c_3$alkyl-ON=CH—, $C_1$–$C_3$alkoxycarbonyl-$C_1$— or —$C_2$alkyl, $C_1$–$C_3$alkylcarbonyl or OHC—.

16. A process for the preparation of a compound of the formula I according to claim 1 in which A-B is a group $$\begin{array}{c} R_2 \\ 2| \quad 3 \\ -C-CH_2-; \\ | \\ R_3 \end{array}$$

$R_2$ is as defined in claim 1; and $R_3$ is $C_1$–$C_6$alkyl, which comprises reacting a compound of the formula II (II)

in which R, $R_1$ and W are as defined in claim 1 with a compound of the formula III (III)

$$\begin{array}{c} R_8 \\ | \\ CH_2=C-CH-L_1 \\ | \\ R_2 \end{array}$$

in which $R_2$ is as defined above; $R_8$ is hydrogen or $C_1$–$C_5$alkyl; and $L_1$ is a leaving group, if appropriate in the presence of an inert organic solvent and of a base, to give the compound of the formula IVa (IVa)

in which R, $R_1$, $R_2$, $R_8$ and W are as defined above, subjecting this compound to a rearrangement reaction, either with exposure to heat or with acid catalysis, to give the compound of the formula Va (Va)

and subsequently cyclizing the latter.

17. A process for the preparation of a compound of the formula I according to claim 1 in which A-B is a group $$\begin{array}{c} R_2 \\ 2| \quad 3 \\ -C-CH_2-; \\ | \\ R_3 \end{array}$$

$R_2$ is defined in claim 1 and $R_3$ is hydroxy-$C_1$–$C_6$alkyl, which comprises epoxidizing a compound of the formula Va (Va)

in which R, $R_1$, $R_2$ and W are as defined in claim 1; and $R_8$ is hydrogen or $C_1$–$C_5$alkyl, and subsequently, if desired, cyclizing the product in the presence of a catalyst.

18. A process for the preparation of a compound of the formula I as claimed in claim 1 in which A-B is a group $$\begin{array}{c} 2 \quad 3 \\ -C=CH-; \\ | \\ R_3 \end{array}$$

and $R_3$ is $C_1$–$C_6$alkyl, which comprises subjecting a compound of the formula IVb

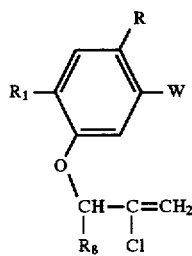 (IVb)

in which R, R₁ and W are as defined in claim 1; and R₈ is hydrogen or $C_1$–$C_5$alkyl to a rearrangement reaction with exposure to heat to give the compound of the formula Vb

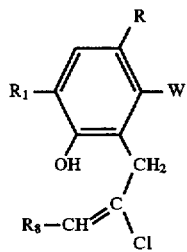 (Vb)

and subsequently cyclizing the latter.

19. A process for the preparation of a compound of the formula I according to claim 1 in which W is a group

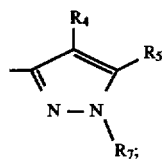 (W1)

R₄ is hydrogen, fluorine, chlorine or bromine; R₅ is $C_1$–$C_6$alkoxycarbonyl, NH₂C(O)— or cyano; and R₇ is hydrogen or $C_1$–$C_4$alkyl, which comprises diazotizing a compound of the formula VI

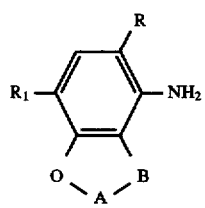 (VI)

in which R, R₁ and A-B have the meaning given in claim 1, replacing the diazonium group by a halogen in the presence of a copper(I) salt, thus obtaining the compound of the formula VII

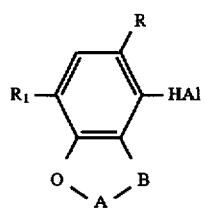 (VII)

in which Hal is halogen, reacting this compound in the presence of palladium(II) chloride, triphenylphosphine and n-butyl vinyl ether to give the compound of the formula VIII

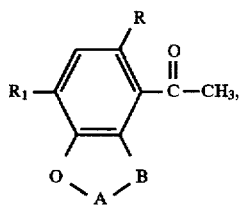 (VIII)

subsequently reacting this compound with a dialkyloxalate of the formula IX

 (IX)

in which R₉ is $C_1$–$C_6$alkyl, in the presence of a base, to give the compound of the formula X

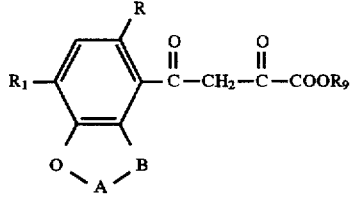 (X)

cyclizing the latter in the presence of hydrazine to give the compound of the formula Ia

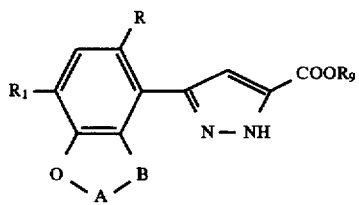 (Ia)

subsequently converting the latter first with an alkylating reagent of the formula XIIa

 (XIIa)

or of the formula XIIb

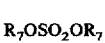 (XIIb)

where the radical R₇ in the compounds of the formulae XIIa and XIIb is $C_1$–$C_4$alkyl and L₂ is a leaving group to give the compound of the formula Ib

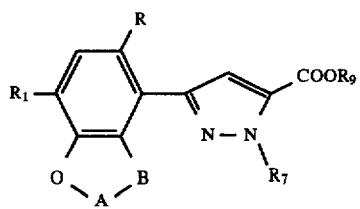 (Ib)

in which R, R₁, R₇, R₉ and A-B are as defined above, and subsequently subjecting the product to a halogenation reaction, thus obtaining the compound of the formula Ic

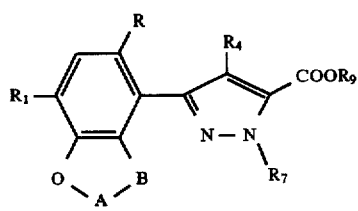 (Ic)

in which R, $R_1$, $R_7$, $R_9$ and A-B are as defined above; and $R_4$ is fluorine, chlorine or bromine, and reacting this compound either directly or via the corresponding carboxylic acid or the corresponding carboxylic acid halide of the formula $Ic_1$

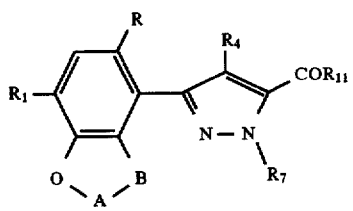 ($Ic_1$)

in which R, $R_1$, $R_4$, $R_7$ and A-B are as defined above; and $R_{11}$ is hydroxyl or halogen, with ammonia to give the amide of the formula Id

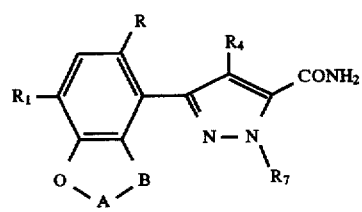 (Id)

and subsequently dehydrating the latter.

20. A process for the preparation of a compound of the formula I according to claim 1 in which W is a group

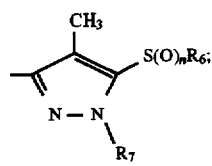 (W2)

$R_6$, $R_7$ and n are as defined in claim 1, which comprises a) cyclizing a compound of the formula XI

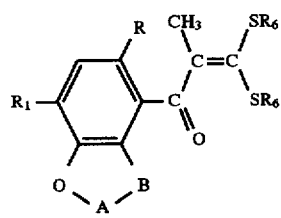 (XI)

in which R, $R_1$, $R_6$ and A-B are as defined in claim 1 with hydrazine, in the presence or absence of a suitable solvent, to give the compound of the formula Ie

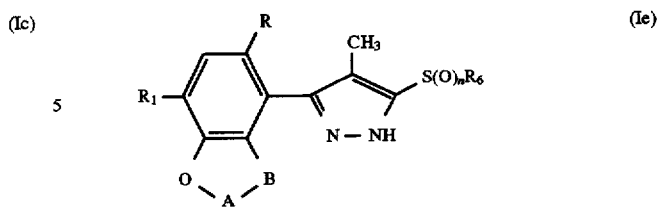 (Ie)

in which n is 0 and subsequently reacting this compound with a compound of the formula XIIa

 (XIIa)

or of the formula XIIb

 (XIIb)

the radical $R_7$ in the compounds of the formulae XIIa and XIIb being $C_1$–$C_4$alkyl and $L_2$ being a leaving group to give the compound of the formula If

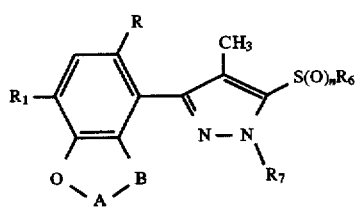 (If)

in which R, $R_1$, $R_6$, $R_7$ and A-B are as defined above; and n is 0, and subsequently oxidizing the product; or b) cyclizing a compound of the formula XIII

 (XIII)

in which $R_7$ is as defined above, in the presence or absence of a suitable solvent, to give the compound of the formula If and subsequently oxidizing this compound.

21. A process for the preparation of a compound of the formula I according to claim 1 in which W is a

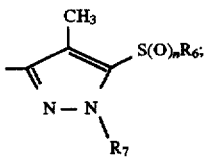 (W2)

$R_7$ is hydrogen; and $R_6$ and n are as defined in claim 1, which comprises halogenating a compound of the formula VIIIa

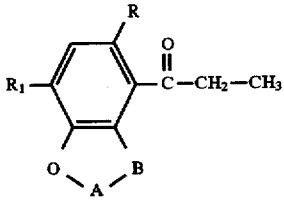 (VIIIa)

in the presence or absence of a solvent and of a base, to give the compound of the formula XIV

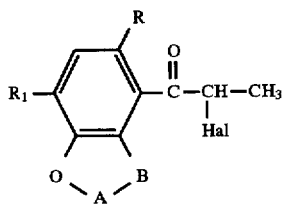

R, R₁ and A-B in the compounds of the formulae VIIIa and XIV being as defined in claim 1 and Hal being halogen and cyclizing this compound with the compound of the formula XV

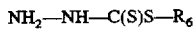

in which R₆ is as defined above, in the presence or absence of a solvent and of a base, to give the compound of the formula XVI

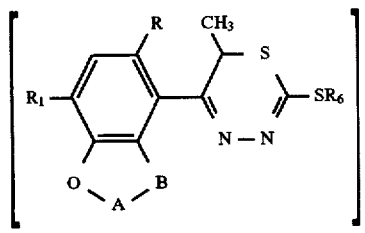

and subjecting the latter to a ring contraction (n=0), either with exposure to heat or with acid catalysis, and subsequently oxiding the product (n=1 or 2).

22. A herbicidal and plant-growth-inhibiting composition, which comprises a herbicidally effective amount of compound of the formula I according to claim 1 and an inert carrier.

23. A composition according to claim 22, which comprises between 0.1% and 95% of active ingredient of the formula I.

24. A method of controlling undesirable plant growth, which comprises applying a herbicidally active amount of an active ingredient of the formula I according to claim 1 or of a composition which comprises this active ingredient to the plants or their environment.

25. A method according to claim 24, which comprises applying an amount of active ingredient of between 0.001 and 4 kg per hectare.

26. A method of inhibiting plant growth, which comprises applying an effective amount of an active ingredient of the formula I according to claim 1 or of a composition which comprises this active ingredient to the plants or their environment.

* * * * *